United States Patent [19]
Bauer et al.

[11] Patent Number: 6,001,959
[45] Date of Patent: Dec. 14, 1999

[54] **HYPERSENSITIVE RESPONSE ELICITOR FROM *ERWINIA CHRYSANTHEMI***

[75] Inventors: David Bauer; Alan Collmer, both of Ithaca, N.Y.

[73] Assignee: Cornell Research Foundation, Inc., Ithaca, N.Y.

[21] Appl. No.: 09/118,959

[22] Filed: Jul. 17, 1998

Related U.S. Application Data

[62] Division of application No. 08/484,358, Jun. 7, 1995, Pat. No. 5,850,015.

[51] Int. Cl.$^6$ ........................... C12N 15/00; C12N 15/09; C12N 15/11; A01N 63/00
[52] U.S. Cl. ........................ 530/300; 435/69.1; 800/298; 800/300.1
[58] Field of Search ................................ 800/298, 300.1; 435/69.1; 530/300

[56] References Cited

U.S. PATENT DOCUMENTS

| | | |
|---|---|---|
| 4,569,841 | 2/1986 | Liu . |
| 4,597,972 | 7/1986 | Taylor . |
| 4,601,842 | 7/1986 | Caple et al. . |
| 4,740,593 | 4/1988 | Gonzales et al. . |
| 4,851,223 | 7/1989 | Sampson . |
| 4,886,825 | 12/1989 | Ruess et al. . |
| 4,931,581 | 6/1990 | Schurter et al. . |
| 5,061,490 | 10/1991 | Paau et al. . |
| 5,135,910 | 8/1992 | Blackburn et al. . |
| 5,173,403 | 12/1992 | Tang . |
| 5,217,950 | 6/1993 | Blackburn et al. . |
| 5,243,038 | 9/1993 | Ferrari et al. . |
| 5,244,658 | 9/1993 | Parke . |
| 5,260,271 | 11/1993 | Blackburn et al. . |
| 5,348,743 | 9/1994 | Ryals et al. . |
| 5,494,684 | 2/1996 | Cohen . |
| 5,523,311 | 6/1996 | Schurter et al. . |
| 5,550,228 | 8/1996 | Godiard et al. . |
| 5,552,527 | 9/1996 | Godiard et al. . |

FOREIGN PATENT DOCUMENTS

| | | |
|---|---|---|
| WO 94/01546 | 1/1994 | WIPO . |
| WO 94/26782 | 11/1994 | WIPO . |

OTHER PUBLICATIONS

Wei et al. Science vol. 257, pp. 85–88, Jul. 1992.
Bauer et al. Sixth International Symposium on Molecular Plant Microbe Interactions, Abstract No. 146, Jul. 1992.
Stryer, "Enzymes are Highly Specific," *Biochemistry*, San Francisco: W.H. Freeman and Company, p. 116 (1975).
Keen et al., "Inhibition of the Hypersensitive Reaction of Soybean Leaves to Incompatible *Pseudomonas* spp. by Blasticidin S, or Elevated Temperature," *Physiological Plant Pathology*, 18:325–337 (1981).
Lerner "Tapping the Immunological Repertoire to Produce Antibodies of Predetermined Specificity," *Nature*, 299:592–596 (1982).
Staskawicz et al., "Cloned Avirulence Gene of *Pseudomonas syringae* pv. *glycinea* Determines Race–specific Incompatibility on *Glycine max* (L.) Merr.," *Proc. Natl. Acad. Sci.*, 81:6024–6028 (1984).
Atkinson et al., "The Hypersensitive Reaction of Tobacco to *Pseudomonas syringae* pv. *pisi*$^1$," *Plant Physiol.*, 79:843–847 (1985).
Huynh et al., "Bacterial Blight of Soybean: Regulation of a Pathogen Gene Determining Host Cultivar Specificity," *Science*, 245:1374–1377 (1986).
Lindgren et al., "Gene Cluster of *Pseudomonas syringae* pv. "Phaselicola" *J. Bacteriology*, Controls Pathogenicity of Bean Plants and Hypersensitivity on Nonhost Plant," 168(2):512–522 (1986).
Bauer et al., "Cloning of a Gene from *Erwinia amylovora* Involved in Induction of Hypersensitivity and Pathogenicity," *Plant Pathogenic Bacteria*, 425–429 (1987).
Collinge et al., "Plant Gene Expression in Response to Pathogens," *Plant Molecular Biology*, 9:389–410 (1987).
Shatzman et al., "Expression, Identification, and Characterization of Recombinant Gene Products in *Escherichia coli*," *Methods in Enzymology*, 1562:661–673 (1987).
Shields, "Towards Insect–Resistant Plants," *Nature* 328:12–13 (1987).
Huang et al., "Molecular Cloning of a *Pseudomonas syringae* pv. *syringae* Gene Cluster That Enables *Pseudomonas fluorescens* To Elicit the Hypersensitive Response in Tobacco Plants," *Journal of Bacteriology*, 170(10):4748–4756 (1988).
Schottens–Toma et al., "Purification and Primary Structure of a Necrosis–inducing Peptide from the Apoplastic Fluids of Tomato Infected with *Cladosporium fulvum* (syn. Fulvia fulva)," *Physiological and Molecular Plant Pathology*, 33:59–67 (1988).
Steinberger et al., "Creation and Complementation of Pathogenicity Mutants of *Erwinia amylovara*," *Molecular Plant–Microbe Interactions*, 1(3):135–144 (1988).
Beer et al., "The Hypersensitive Response is Elicited by *Escherichia coli* Containing a Cluster of Pathogenicity Genes from *Erwinia amylovara*," *Phytopathology*, 79(10):1156 (Abstract 169) (1989).
Hiatt et al., Production of Antibodies in Transgenic Plants, *Nature*, 342:76–78 (1989).

(List continued on next page.)

*Primary Examiner*—Lynette R. F. Smith
*Assistant Examiner*—Thomas Haas
*Attorney, Agent, or Firm*—Nixon Peabody LLP

[57] ABSTRACT

The present invention relates to an isolated protein or polypeptide corresponding to a protein or polypeptide in *Erwinia chrysanthemi* which elicits a hypersensitive response in plants. The encoding DNA molecule alone in isolated form or either in an expression system, a host cell, or a transgenic plant are also disclosed. Another aspect of the present invention relates to a method of imparting pathogen resistance to plants by transforming a plant with the DNA molecule of the present invention.

5 Claims, 6 Drawing Sheets

OTHER PUBLICATIONS

Hippe et al., "In Situ Localization of a Foreign Protein in Transgenic Plants by Immunoelectron Microscopy Following High Pressure Freeze Substitution and Low Temperature Embedding," *European Journal of Cell Biology*, 50:230–234 (1989).

Huang et al., "Isolation and Purification of a Factor from *Pseudomonas solanacearum* That Induces a Hypersensitive– like Response in Potato Cells," *Molecular Plant–Microbe Interactions*, 2(3):132–138 (1989).

James et al., "Genetic Transformation of Apple (*Malus pumila* Mill.) Using a Disarmed Ti–binary Vector," *Plant Cell Reports*, 7:658–661 (1989).

Laby et al., "Cloning and Preliminary Characterization of an HRP Gene Cluster of *Erwinia amylovora*," *Phytopathology*, 79(10):1211 (Abstract 607) (1989).

Dow et al., "Extracellular Proteases from *Xanthomonas campestris* pv. Campestris, the Black Rot Pathogen," *Applied and Environmental Microbiology*, 56(10):2994–2998 (1990).

Walters et al., "Gene for Pathogenicity and Ability to Cause the Hypersensitive Reaction Cloned from *Erwinia amylovora*," *Physiological and Molecular Plant Pathology*, 36:509–521 (1990).

Wu et al., "Cloning, Genetic Organization, and Characterization of a Structural Gene Encoding Bacillopeptidase F from *Bacillus subtilis*," *The Journal of Biological Chemistry*, 265(12):6845–6850 (1990).

Bauer et al., "Further Characterization of an hrp Gene Cluster of *Erwinia amylovora*," *Molecular Plant Microbe Interactions*, 4(5):493–499 (1991).

Beer et al., "The HRP Gene Cluster of *Erwinia amylovora*," *Advances in Molecular Genetics of Plant–Microbe Interactions*, 1:53–60 (1991).

Benvenuto et al., "'Phytoantibodies': A General Vector for the Expression of Immunoglobulin Domains in Transgenic Plants," *Plant Molecular Biology*, 17:865–874 (1991).

Milat et al., "Physiological and Structural Changes in Tobacco Leaves Treated with Cryptogein, a Proteinaceous Elicitor from *Phytophthora cryptogea*," *Phytopathology*, 81(11):1364–1368 (1991).

Ruberti et al., "A Novel Class of Plant Proteins Containing a Homeodomain with a Closely Linked Leucine Zipper Motif," *The EMBO Journal*, 10(7):1787–1791 (1991).

Quigley et al., "Nucleotide Sequence and Expression of a Novel Glycine–Rich Protein Gene from *Arabidopsis thaliana*," *Plant Molecular Biology*, 17:979–952 (1991).

van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1):52–59 (1991).

Waldmann, "Monoclonal Antibodies and Therapy," *Science*, 252:1657–1662 (1991).

Willis et al., "hrp Genes of Phytopathogenic Bacteria," *Molecular Plant–Microbe Interactions*, 4:(2) 132–138 (1991).

Beer et al., "Are Harpins Universal Elicitors of the Hypersensitive Response of Phytopathogenic Bacteria?," *Advances in Molecular Genetics of Plant–Microbe Interactions*, 2:281–286 (1992).

Laby et al., *Molecular Plant–Microbe Interactions*, 5(5):412 (1992).

Sandhu, *Crit. Rev. in Biotech.*, (92–review) 12:437–462.

Wei et al., "Harpin, Elicitor of the Hypersensitive Response Produced by the Plant Pathogen *Erwinia amylovora*," *Science*, 257:85–88 (1992).

He et al., "*Pseudomonas syringae* pv. syringae Harpin$_{P86}$: A Protein that is Secreted Via the Hrp Pathway and Elicits the Hypersensitive Response in Plants," *Cell*, 73:1255–1266 (1993).

Bonas, "Bacterial Home Goal by Harpins," *Trends in Microbiology*, 2:1–2 (1994).

Collmer et al., "*Erwinia chrysanthemi* and *Pseudomonas syringae*: Plant Pathogens Trafficking in Extracellular Virulence Proteins," pp. 43–78.

Frederick et al., "The WTS Water–Soaking Genes of *Erwinia stewartii* are Related to hrp Genes," Seventh International Symposium on Molecular Plant Microbe Interactions, Abstract No. 191 (Jun. 1994).

Wei et al., "Proteinaceous Elicitor of the Hypersensitive Response from *Xanthomonas campestris* pv. *glycines*," Seventh International Symposium on Molecular Plant Microbe Interactions, Abstact No. 244 (Jun. 1994).

Preston et al., "The HrpZ Proteins of *Pseudomonas syringae* pvs. *syringae, glycinea*, and *tomato* are Encoded by an Operon Containing Yersinia ysc Honologs and Elicit the Hypersensitive Response to Tomato but not Soybean," *Mol. Plant–Microbe Interact.*, 8:717–732 (1995).

Bauer et al., "*Erwinia chrysanthemi* hrp Genes and their Involvement in Elicitation of the Hypersensitive Response in Tobacco," Sixth International Symposium on Molecular Plant Microbe Interactions, Abstract No. 146 (Jul. 1992).

Bauer et al., "*Erwinia chrysanthemi* Harpin$_{Ech}$: An Elicitor of the Hypersensitive Response that Contributes to Soft–Rot Pathogenesis," *MPMI*, 8(4):484–491 (1995).

Huang et al., "Characterization of the hrp Cluster from *Pseudomonas syringae* pv. *syringae* 61 and TnphoA Tagging of Genes Encoding Exported or Membrane–Spanning Hrp Proteins," *Molec. Plant–Microbe Interact.*, 4(5):469–476 (1991).

Huang et al., "The *Pseudomonas syringae* pv. *syringae* 61 hrpH Product, and Envelope Protein Required for Elicitation of the Hypersensitive Response in Plants," *J. of Bacteriology*, 174(21):6878–6885 (1992).

Bonas, "hrp Genes of Phytopathogenic Bacteria," *Current Topics in Microbiology and Immunology*, 192:79–98 (1994).

Ariat et al., "PopA1, A Protein Which Induces a Hypersensitivity–Like Response on Specific Protein Petunia Genotypes is Secreted Via the Hrp Pathway of *Pseudomonas solanacearum*," *The EMBO Journal.*, 13(3):543–553 (1994).

Kessman et al., "Induction of Systemic Acquired Disease Resistance in Plants By Chemicals," *Annu. Rev. Phytopathol.*, 32:439–59 (1994).

Kelman, "The Relationship of Pathogenicity in *Pseudomonas solanacearum* To Colony Appearance on a Tetrazolium Medium," *Phytopathology*, 44:693–695 (1954).

Winstead et al., "Inoculation Techniques For Evaluating Resistance to Pseudomonas Solanacearum," *Phytopathology*, 42:628–634 (1952).

Ahl et al., "Iron Bound–Siderophores, Cyanic Acid, and Antibodies Involved in Suppression of *Thielaviopsis basiocola* by a *Pseudomonas fluorescens* Strain," *J. Pathology*, 116:121–134 (1986).

Anderson et al., "Responses of Bean to Root Colonization with *Pseudomonas putida* in a Hydroponic System," *Phytopathology*, 75(9):992–995 (1985).

Gardner et al., "Growth Promotion and Inhibition by Antibiotic–Producing Fluorescent Pseudomonads on Citrus Roots," *Plant and Soil*, 77:103–113 (1984).

Kloepper, "Effect of Seed Piece Inoculation with Plant Growth–Promoting Rhizobacteria on Populations of *Erwinia carotovora* on Potato Roots and In Daughter Tubers," *Phytopathology*, 73(2):217–219 (1983).

Kloepper et al., "Plant Growth–Promoting Rhizobacteria on Canola (Rapeseed)," *Plant Disease* 72(1):42–46 (1988).

Kloepper et al., "Enhanced Plant Growth by Siderophores Produced by Plant Growth–Promoting Rhizobacteria," *Nature*, 286:885–886 (1980).

Kloepper et al., "Pseudomonas Siderophores: A Mechanism Explaining Disease–Suppressive Soils," *Current Microbiology*, 4:317–320 (1980).

Kloepper et al., "Emergence–Promoting Rhizobacteria: Description and Implications for Agriculture," *Iron, Siderophores, and Plant Disease*, Swinborne (ed), Plenum, NY, 155–164 (1986).

Kloepper et al., "Relationships of in vitro Antibiosis of Plant Growth–Promoting Rhizobacteria to Plant Growth and the Displacement of Root microflora," *Phytopathology*, 71(10):1020–1024 (1981).

Kloepper et al., "Effects of Rhizosphere Colonization by Plant Growth–Promoting Rhizobacteria on Potato Plant Development and Yield," *Phytopathology*, 70(11):1078–1082 (1980).

Kloepper et al., "Plant Growth Promotion Mediated by Rhizosphere Bacterial Colonizers," *The Rhizosphere and Plant Growth*, Keister et al. (eds). 315–326 (1991).

Lifshitz et al., "Growth Promotion of Canola (rapeseed) by a Strain Seedlings of *Pseudomonas putida* Under Gnotobiotic Conditions," *Microbiol.* 33:390–395 (1987).

Liu et al., "Induction of Systemic Resistance in Cucumber Against Bacterial Angular Leaf Spot by Plant Growth–Promoting Rhizobacteria," *Phytopathology*, 85(8):843–847 (1995).

Loper et al., "Influence of Bacterial Sources of Indole–3–acetic Acid on Root Elongation of Sugar Beet," *Phytopathology*, 76(4):386–389 (1986).

Schroth et al., "Disease–Suppressive Soil and Root–Colonizing Bacteria," *Science*, 216:1376–1381 (1982).

Stutz et al., "Naturally Occurring Fluorescent Pseudomonads Involved in Suppression of Black Root Rot of Tobacco," *Phytopathology*, 76(2):181–185 (1986).

Wei et al., "Induction of Systemic Resistance of Cucumber to *Colletotrichum orbiculare* by Select Strains of Plant Growth–Promoting Rhizobacteria," *Phytopathology*, 81:1508–1512 (1991).

Wei et al., "Induction of Systemic Resistance with seed Treatment by PGPR Strains," pp. 191–194.

Weller, "Biological Control of Soilborne Plant Pathogens in the Rhizosphere with Bacteria," *Ann. Rev. Phytopathol.*, 26:379–407 (1988).

Young et al., "PGPR: Is There a Relationship Between Plant Growth Regulators and the Stimulation of Plant Growth or Biological Activity?," pp. 182–186.

Wei et al., "Induced Systemic Resistance by Select Plant Growtn–Promoting Rhizobacteria Against Bacterial Wilt of Cucumber and the Beetle Vectors," *Phytopathology*, 86:1154, Abstract No. 313 (1995).

Wieringa–Brants et al., Induced Resistance in Hypersensitive Tobacco Mosaic Virus by Injection of Intercellular Fluid from Tobacco Plants with Systemic Acquired Resistance, *Phytopathology*, 118:166–170 (1987).

Malamy et al., "Salicylic Acid: A Likely Endogenous Signal in the Resistance Response of Tobacco to Viral Infection," *Science*, 250:1002–1004 (1990).

Dean et al., "Immunisation Against Disease: The Plant Fights Back," pp. 383–411.

Cameron et al., "Biologically Induced Systemic Acquired Resistance in *Arabidopsis thaliana*," *The Plant Journal*, 5(5):717–725 (1994).

Laby et al., "Structural and Functional Analysis of *Erwinia amylovora* Harpin, An Elicitor of the Plant Hypersensitive Response," *Phytopathology*, 84:345 (1994).

Van Gijsegem et al., "Evolutionary Conservation of Pathogenicity Determinants Among Plant and Animal Pathogenic Bacteria," *Trends Microbiol.*, I:175–180 (1993).

Kamoun et al., "Extracellular Protein Elicitors from Phytophthora: Host–Specificity and Induction of Resistance to Bacterial and Phytopathogens," *Molecular Plant–Microbe Interactions*, 6(1):15–25 (1993).

Baillieul et al., "A New Elicitor of the Hypersensitive Repsonse in Tobacco: A Fungal Glycoprotein Elicits Cell Death, Expression Defense Genes, Production of Salicylic acid, and Induction of Systemic Acquired Resistance," *The Plant Journal*, 8(4):551–60.

Tenhaken et al., "Function of the Oxidative Burst in Hypersensitive Disease Resistance," *Proc. Natl. Acad. Sci. USA*, 92:4158–63 (1995).

Bonnet et al., "Induction de nécroses foliaires, de protéines b et de résistance dans les interactions tabac Phytophthora," *Agronomie*, 6(9):829–37 (1986).

Gallitelli et al., "Satellite–Mediated Protection of Tomato Against Cucumber Mosaic Virus: II. Field Test Under Natural Epidemic Conditions in Southern Italy," *Plant Disease*, 75(1):93–95 (1991).

Ahn et al., "Effects of Chilling Periods on the Growth and Yield of Strawberry (*Fragaria grandifloro* EHRH) in Forcing Culture," 27(1):17–26 (1985).

Montasser et al., "Satellite–Mediated Protection of Tomato Against Cucumber Mosaic Virus: I. Greenhouse Experiments and Stimulated Epidemic Conditions in the Field," *Plant Disease*, 75(1):86–92 (1991).

Marks, R.J., "Varietal Resistance to Potato Cyst Nematode," *Agricultural Entomology*, (1979).

Walton et al., "Host–Selective Toxins and Disease Specificity: Perspectives and Progress," *Annu. Rev. Phytopathol.*, 31:275–303 (1993).

Atkinson M.M., "Molecular Mechanisms of Pathogen Recognition by Plants," *Advances in Plant Pathology*, 10:36–64 (1993).

Godiard et al., "Differential Regulation in Tobacco Cell Suspensions of Genes Involved in Plant–Bacteria Interactions by Pathogen–Related Signals," *Plant Molecular Biology*, 17:409–13 (1991).

Ricci et al., "Structure and Activity of Proteins from Pathogenic Fungi Phytophthora Eliciting Necrosis and Acquired Resistance in Tobacco," *Eur. J. Biochem.* 183:555–63 (1989).

Lakhmatova I.T., "Induction of Plant Resistance to Viral Diseases: Application of Vaccination," *Sel'skokhozyaistvennaya* 3:39–51 (1991).

*Biologicheskii Zhurnal Armenii*, 31(3):305–09 (1978).

Lakhmatova I.T., "Using Biologically Active Substances to Induced Plant Resistance to Viruses Immunization," *Biologiya*, 3:13–22 (1992).

Ricci et al., "Differential Production of Parasiticein, and Elicitor of Necrosis and Resistance in Tobacco, by Isolates of *Phytophthora parasitica*," *Plant Pathology*, 41:298–307 (1992).

Honée et al., "Molecular Characterization of the Interaction Between the Fungal Pathogen *Cladosporium fulvum* and Tomato," *Advances in Molecular Genetics of Plant–Microbe Interactions*, 3:199–206 (1994).

Keller et al., "Responses of Tobacco to Elicitins, Proteins From Phytophthora Spp. Eliciting Acquired Resistance," *Advances in Molecular Genetics of Plant–Microbe Interactions*, 3:327–32 (1994).

Keen et al., "Bacteria Expressing Avirulence Gene D Produce a Specific Elicitor of the Soybean Hypersensitve Reaction," *Molecular Plant–Microbe Interactions*, 3(2):112–21 (1990).

Boccara et al., "Plant Defense Elicitor Protein Produced by *Erwinia chrysanthemi*," *Mech. of Plant Defense Responses*, 166 (1993).

Bauer et al., "*Erwinia chrysanthemi* hrp Genes and Their Involvement in Soft Rot Pathogenesis and Elicitation of The Hypersensitive Response," *MPMI*, 7(5):573–581 (1994).

Beer et al., "Are Harpins Universal Elicitors of the Hypersensitive Response of Phytopathogenic Bacteria?," *Advances in Molecular Genetics of Plant–Microbe Interactions*, 2:281–286 (1992).

```
   1  AATGAGGAAACGAAATTATGCAAATTACGATCAAAGCGCACATCGGCGGTGATTTGGGCG
                   M  Q  I  T  I  K  A  H  I  G  G  D  L  G

61  TCTCCGGTCTGGGGCTGGGTGCTCAGGGACTGAAAGGACTGAATTCCGCGGCTTCATCGC
      V  S  G  L  G  L  G  A  Q  G  L  K  G  L  N  S  A  A  S  S

121  TGGGTTCCAGCGTGGATAAACTGAGCAGCACCATCGATAAGTTGACCTCCGCGCTGACTT
      L  G  S  S  V  D  K  L  S  S  T  I  D  K  L  T  S  A  L  T

181  CGATGATGTTTGGCGGCGCGCTGGCGCAGGGGCTGGGCGCCAGCTCGAAGGGGCTGGGGA
      S  M  M  F  G  G  A  L  A  Q  G  L  G  A  S  S  K  G  L  G

241  TGAGCAATCAACTGGGCCAGTCTTTCGGCAATGGCGCGCAGGGTGCGAGCAACCTGCTAT
      M  S  N  Q  L  G  Q  S  F  G  N  G  A  Q  G  A  S  N  L  L

301  CCGTACCGAAATCCGGCGGCGATGCGTTGTCAAAAATGTTTGATAAAGCGCTGGACGATC
      S  V  P  K  S  G  G  D  A  L  S  K  M  F  D  K  A  L  D  D

361  TGCTGGGTCATGACACCGTGACCAAGCTGACTAACCAGAGCAACCAACTGGCTAATTCAA
      L  L  G  H  D  T  V  T  K  L  T  N  Q  S  N  Q  L  A  N  S
                                                  ↓------>  439::Tn5-gusA1
 421  TGCTGAACGCCAGCCAGATGACCCAGGGTAATATGAATGCGTTCGGCAGCGGTGTGAACA
      M  L  N  A  S  Q  M  T  Q  G  N  M  N  A  F  G  S  G  V  N 481  ACGCACTGTCGTCCATTCTCGGCAACGGTCTCGGCCAGTCGATGAGTGGCTTCTCTCAGC
      N  A  L  S  S  I  L  G  N  G  L  G  Q  S  M  S  G  F  S  Q
      546::Tn5-gusA1 <------↓
 541  CTTCTCTGGGGGCAGGCGGCTTGCAGGGCCTGAGCGGCGCGGGTGCATTCAACCAGTTGG
      P  S  L  G  A  G  G  L  Q  G  L  S  G  A  G  A  F  N  Q  L 601  GTAATGCCATCGGCATGGGCGTGGGGCAGAATGCTGCGCTGAGTGCGTTGAGTAACGTCA
      G  N  A  I  G  M  G  V  G  Q  N  A  A  L  S  A  L  S  N  V 661  GCACCCACGTAGACGGTAACAACCGCCACTTTGTAGATAAAGAAGATCGCGGCATGGCGA
      S  T  H  V  D  G  N  N  R  H  F  V  D  K  E  D  R  G  M  A 721  AAGAGATCGGCCAGTTTATGGATCAGTATCCGGAAATATTCGGTAAACCGGAATACCAGA
      K  E  I  G  Q  F  M  D  Q  Y  P  E  I  F  G  K  P  E  Y  Q 781  AAGATGGCTGGAGTTCGCCGAAGACGGACGACAAATCCTGGGCTAAAGCGCTGAGTAAAC
      K  D  G  W  S  S  P  K  T  D  D  K  S  W  A  K  A  L  S  K 841  CGGATGATGACGGTATGACCGGCGCCAGCATGGACAAATTCCGTCAGGCGATGGGTATGA
      P  D  D  D  G  M  T  G  A  S  M  D  K  F  R  Q  A  M  G  M 901  TCAAAAGCGCGGTGGCGGGTGATACCGGCAATACCAACCTGAACCTGCGTGGCGCGGGCG
      I  K  S  A  V  A  G  D  T  G  N  T  N  L  N  L  R  G  A  G 961  GTGCATCGCTGGGTATCGATGCGGCTGTCGTCGGCGATAAAATAGCCAACATGTCGCTGG
      G  A  S  L  G  I  D  A  A  V  V  G  D  K  I  A  N  M  S  L 1021  GTAAGCTGGCCAACGCCTGATAATCTGTGCTGGCCTGATAAAGCGGAAACGAAAAAAGAG
      G  K  L  A  N  A  *  *

1081  ACGGGGAAGCCTGTCTCTTTTCTTATTATGCGG  1113
```

FIG. 1

```
Ech ........MQITIKAHIGGDLGVSGLGLGAQGLKGLNSAASSLGSSVDKL 42
         .|:.   |||.|.||.||-    .:  ::.|.||  :.:.
Ea  MSLNTSGLGASTMQISIGGAGGNNGL.LGTSRQNAGLGGNSALGLGGGNQ 49

Ech SSTIDKLTSALTSMMF.......GGALAQGLGAS.SKGLGMSNQLGQSFG 84
    ..|::.|.:  ||:||:       ||  ::.|||::  :.|||  |..||::::
Ea  NDTVNQLAGLLTGMMMMMSMMGGGGLMGGGLGGGLGNGLGGSGGLGEGLS 99

Ech NGAQG..ASNLLSVPKSGGDALSKMFDKALDDLLG.............. 117
    |:   .:   ::.| .:...||:..  :.:||: ||
Ea  NALNDMLGGSLNTLGSKGGNNTTSTTNSPLDQALGINSTSQNDDSTSGTD 149

Ech .....HDTVTKLTNQSNQLANSMLNAS...........QMTQGNMNAFG 150
         |.:  .|  .  .::  .|::..:           |  |:|  ||:
Ea  STSDSSDPMQQLLKMFSEIMQSLFGDGQDGTQGSSSGGKQPTEGEQNAYK 199

Ech SGVNNALSSILGNLGQSMS..............GFSQPSLGAGGLQGLS 186
    .||.:|||:::|||||:| ::           |:...|||: ||.|||
Ea  KGVTDALSGLMGNGLSQLLGNGGLGGGQGGNAGTGLDGSSLGGKGLRGLS 249

Ech GAGAFNQLGNAIGMGVGQNAALSALSNVSTHVDGNNRHFVDKEDRGMAKE 236
    |:..:.|||||:| |:| .|::  ||.:::||  .:..| ||:|:||:||||
Ea  GPVDYQQLGNAVGTGIGMKAGIQALNDIGTHRHSSTRSFVNKGDRAMAKE 299

Ech IGQFMDQYPEIFGKPEYQKDGWSSPKTDDKSWAKALSKPDDDGMTGASMD 286
    ||||||||||:||||:|||:-    ..||||||||||||||||||||.|||:
Ea  IGQFMDQYPEVFGKPQYQKGPGQEVKTDDKSWAKALSKPDDDGMTPASME 349

Ech KFRQAMGMIKSAVAGDTGNTNLNLRGAGGASLGIDAAVVGDKIANMSLGK 336
    .|..|.||||.::|||||.||:      ||..|.  :  .|.
Ea  QFNKAKGMIKRPMAGDTGNGNLH.........DAVPVVLRWVLMP... 385

Ech LANA 340
```

FIG. 2

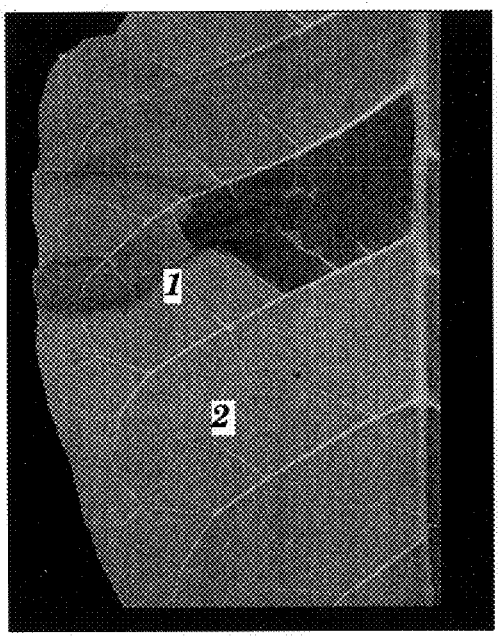
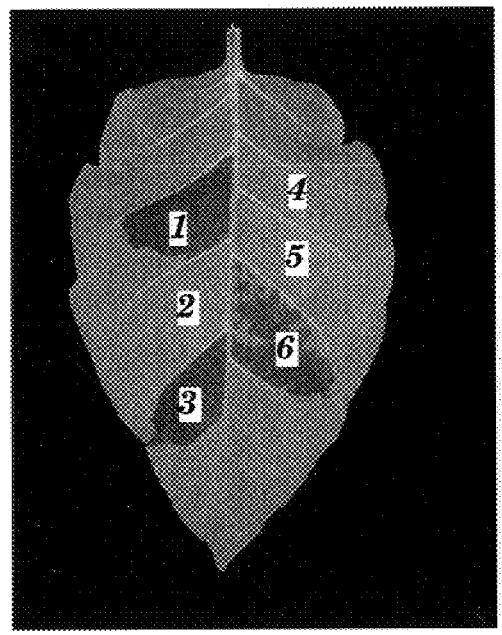
*FIG. 4*  *FIG. 5*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 2141 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
CGATTTTACC CGGGTGAACG TGCTATGACC GACAGCATCA CGGTATTCGA CACCGTTACG      60

GCGTTTATGG CCGCGATGAA CCGGCATCAG GCGGCGCGCT GGTCGCCGCA ATCCGGCGTC     120

GATCTGGTAT TTCAGTTTGG GGACACCGGG CGTGAACTCA TGATGCAGAT TCAGCCGGGG     180

CAGCAATATC CCGGCATGTT GCGCACGCTG CTCGCTCGTC GTTATCAGCA GGCGGCAGAG     240

TGCGATGGCT GCCATCTGTG CCTGAACGGC AGCGATGTAT TGATCCTCTG GTGGCCGCTG     300

CCGTCGGATC CCGGCAGTTA TCCGCAGGTG ATCGAACGTT TGTTTGAACT GGCGGGAATG     360

ACGTTGCCGT CGCTATCCAT AGCACCGACG GCGCGTCCGC AGACAGGGAA CGGACGCGCC     420

CGATCATTAA GATAAAGGCG GCTTTTTTTA TTGCAAAACG GTAACGGTGA GGAACCGTTT     480

CACCGTCGGC GTCACTCAGT AACAAGTATC CATCATGATG CCTACATCGG GATCGGCGTG     540

GGCATCCGTT GCAGATACTT TTGCGAACAC CTGACATGAA TGAGGAAACG AAATTATGCA     600
```

```
AATTACGATC AAAGCGCACA TCGGCGGTGA TTTGGGCGTC TCCGGTCTGG GGCTGGGTGC      660

TCAGGGACTG AAAGGACTGA ATTCCGCGGC TTCATCGCTG GGTTCCAGCG TGGATAAACT      720

GAGCAGCACC ATCGATAAGT TGACCTCCGC GCTGACTTCG ATGATGTTTG GCGGCGCGCT      780

GGCGCAGGGG CTGGGCGCCA GCTCGAAGGG GCTGGGGATG AGCAATCAAC TGGGCCAGTC      840

TTTCGGCAAT GGCGCGCAGG GTGCGAGCAA CCTGCTATCC GTACCGAAAT CCGGCGGCGA      900

TGCGTTGTCA AAAATGTTTG ATAAAGCGCT GGACGATCTG CTGGGTCATG ACACCGTGAC      960

CAAGCTGACT AACCAGAGCA ACCAACTGGC TAATTCAATG CTGAACGCCA GCCAGATGAC     1020

CCAGGGTAAT ATGAATGCGT TCGGCAGCGG TGTGAACAAC GCACTGTCGT CCATTCTCGG     1080

CAACGGTCTC GGCCAGTCGA TGAGTGGCTT CTCTCAGCCT TCTCTGGGGG CAGGCGGCTT     1140

GCAGGGCCTG AGCGGCGCGG GTGCATTCAA CCAGTTGGGT AATGCCATCG GCATGGGCGT     1200

GGGGCAGAAT GCTGCGCTGA GTGCGTTGAG TAACGTCAGC ACCCACGTAG ACGGTAACAA     1260

CCGCCACTTT GTAGATAAAG AAGATCGCGG CATGGCGAAA GAGATCGGCC AGTTTATGGA     1320

TCAGTATCCG GAAATATTCG GTAAACCGGA ATACCAGAAA GATGGCTGGA GTTCGCCGAA     1380

GACGGACGAC AAATCCTGGG CTAAAGCGCT GAGTAAACCG GATGATGACG GTATGACCGG     1440

CGCCAGCATG GACAAATTCC GTCAGGCGAT GGGTATGATC AAAAGCGCGG TGGCGGGTGA     1500

TACCGGCAAT ACCAACCTGA ACCTGCGTGG CGCGGGCGGT GCATCGCTGG GTATCGATGC     1560

GGCTGTCGTC GGCGATAAAA TAGCCAACAT GTCGCTGGGT AAGCTGGCCA ACGCCTGATA     1620

ATCTGTGCTG GCCTGATAAA GCGGAAACGA AAAAGAGAC GGGGAAGCCT GTCTCTTTTC      1680

TTATTATGCG GTTTATGCGG TTACCTGGAC CGGTTAATCA TCGTCATCGA TCTGGTACAA     1740

ACGCACATTT TCCCGTTCAT TCGCGTCGTT ACGCGCCACA ATCGCGATGG CATCTTCCTC     1800

GTCGCTCAGA TTGCGCGGCT GATGGGGAAC GCCGGGTGGA ATATAGAGAA ACTCGCCGGC     1860

CAGATGGAGA CACGTCTGCG ATAAATCTGT GCCGTAACGT GTTTCTATCC GCCCCTTTAG     1920

CAGATAGATT GCGGTTTCGT AATCAACATG GTAATGCGGT TCCGCCTGTG CGCCGGCCGG     1980

GATCACCACA ATATTCATAG AAAGCTGTCT TGCACCTACC GTATCGCGGG AGATACCGAC     2040

AAAATAGGGC AGTTTTTGCG TGGTATCCGT GGGGTGTTCC GGCCTGACAA TCTTGAGTTG     2100

GTTCGTCATC ATCTTTCTCC ATCTGGGCGA CCTGATCGGT T                        2141
```

(2) INFORMATION FOR SEQ ID NO:2:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gln Ile Thr Ile Lys Ala His Ile Gly Gly Asp Leu Gly Val Ser
 1               5                  10                  15

Gly Leu Gly Ala Gln Gly Leu Lys Gly Leu Asn Ser Ala Ala Ser Ser
                20                  25                  30

Leu Gly Ser Ser Val Asp Lys Leu Ser Ser Thr Ile Asp Lys Leu Thr
            35                  40                  45

Ser Ala Leu Thr Ser Met Met Phe Gly Gly Ala Leu Ala Gln Gly Leu
        50                  55                  60

Gly Ala Ser Ser Lys Gly Leu Gly Met Ser Asn Gln Leu Gly Gln Ser
65                  70                  75                  80
```

```
Phe Gly Asn Gly Ala Gln Gly Ala Ser Asn Leu Leu Ser Val Pro Lys
                 85                  90                  95
Ser Gly Gly Asp Ala Leu Ser Lys Met Phe Asp Lys Ala Leu Asp Asp
            100                 105                 110
Leu Leu Gly His Asp Thr Val Thr Lys Leu Thr Asn Gln Ser Asn Gln
            115                 120                 125
Leu Ala Asn Ser Met Leu Asn Ala Ser Gln Met Thr Gln Gly Asn Met
130                 135                 140
Asn Ala Phe Gly Ser Gly Val Asn Asn Ala Leu Ser Ser Ile Leu Gly
145                 150                 155                 160
Asn Gly Leu Gly Gln Ser Met Ser Gly Phe Ser Gln Pro Ser Leu Gly
                165                 170                 175
Ala Gly Gly Leu Gln Gly Leu Ser Gly Ala Gly Ala Phe Asn Gln Leu
            180                 185                 190
Gly Asn Ala Ile Gly Met Gly Val Gly Gln Asn Ala Ala Leu Ser Ala
            195                 200                 205
Leu Ser Asn Val Ser Thr His Val Asp Gly Asn Asn Arg His Phe Val
210                 215                 220
Asp Lys Glu Asp Arg Gly Met Ala Lys Glu Ile Gly Gln Phe Met Asp
225                 230                 235                 240
Gln Tyr Pro Glu Ile Phe Gly Lys Pro Glu Tyr Gln Lys Asp Gly Trp
                245                 250                 255
Ser Ser Pro Lys Thr Asp Asp Lys Ser Trp Ala Lys Ala Leu Ser Lys
            260                 265                 270
Pro Asp Asp Asp Gly Met Thr Gly Ala Ser Met Asp Lys Phe Arg Gln
            275                 280                 285
Ala Met Gly Met Ile Lys Ser Ala Val Ala Gly Asp Thr Gly Asn Thr
290                 295                 300
Asn Leu Asn Leu Arg Gly Ala Gly Gly Ala Ser Leu Gly Ile Asp Ala
305                 310                 315                 320
Ala Val Val Gly Asp Lys Ile Ala Asn Met Ser Leu Gly Lys Leu Ala
                325                 330                 335
Asn Ala
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TGACCTGCAG CCAAGCTTTC C                                                21

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AGTACCATGG TTATTACGAT CAAAGCGCAC                                 30

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
AGATCTCGAG GGCGTTGGCC AGCTTACC                                    28
```

(2) INFORMATION FOR SEQ ID NO:6:

(i) SEQUENCE CHARACTERISTICS:
        (A) LENGTH: 1023 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
ATGCAAATTA CGATCAAAGC GCACATCGGC GGTGATTTGG GCGTCTCCGG TCTGGGGCTG    60

GGTGCTCAGG GACTGAAAGG ACTGAATTCC GCGGCTTCAT CGCTGGGTTC CAGCGTGGAT   120

AAACTGAGCA GCACCATCGA TAAGTTGACC TCCGCGCTGA CTTCGATGAT GTTTGGCGGC   180

GCGCTGGCGC AGGGGCTGGG CGCCAGCTCG AAGGGGCTGG GGATGAGCAA TCAACTGGGC   240

CAGTCTTTCG GCAATGGCGC GCAGGGTGCG AGCAACCTGC TATCCGTACC GAAATCCGGC   300

GGCGATGCGT TGTCAAAAAT GTTTGATAAA GCGCTGGACG ATCTGCTGGG TCATGACACC   360

GTGACCAAGC TGACTAACCA GAGCAACCAA CTGGCTAATT CAATGCTGAA CGCCAGCCAG   420

ATGACCCAGG GTAATATGAA TGCGTTCGGC AGCGGTGTGA ACAACGCACT GTCGTCCATT   480

CTCGGCAACG GTCTCGGCCA GTCGATGAGT GGCTTCTCTC AGCCTTCTCT GGGGGCAGGC   540

GGCTTGCAGG GCCTGAGCGG CGCGGGTGCA TTCAACCAGT TGGGTAATGC CATCGGCATG   600

GGCGTGGGGC AGAATGCTGC GCTGAGTGCG TTGAGTAACG TCAGCACCCA CGTAGACGGT   660

AACAACCGCC ACTTTGTAGA TAAAGAAGAT CGCGGCATGG CGAAAGAGAT CGGCCAGTTT   720

ATGGATCAGT ATCCGGAAAT ATTCGGTAAA CCGGAATACC AGAAAGATGG CTGGAGTTCG   780

CCGAAGACGG ACGACAAATC CTGGGCTAAA GCGCTGAGTA AACCGGATGA TGACGGTATG   840

ACCGGCGCCA GCATGGACAA ATTCCGTCAG GCGATGGGTA TGATCAAAAG CGCGGTGGCG   900

GGTGATACCG GCAATACCAA CCTGAACCTG CGTGGCGCGG GCGGTGCATC GCTGGGTATC   960

GATGCGGCTG TCGTCGGCGA TAAAATAGCC AACATGTCGC TGGGTAAGCT GGCCAACGCC  1020

TGA                                                              1023
```

HYPERSENSITIVE RESPONSE ELICITOR FROM *ERWINIA CHRYSANTHEMI*

This application is a division of U.S. patent application Ser. No. 08/484,358, filed Jun. 7, 1995 now U.S. Pat. No. 5,850,015.

This work was supported by NRI Competitive Grants Program/USDA grants 91-37303-6321 and 94-37303-0734.

FIELD OF THE INVENTION

The present invention relates to the Hypersensitive Response Elicitor from *Erwinia chrysanthemi* and its uses.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

The hypersensitive response is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise*, Vol. 5, J. G. Horsfall and E. B. Cowling, ed. Academic Press New York (1980); Klement, Z., "Hypersensitivity," pages 149–177 in: *Phytopathogenic Prokaryotes*, Vol. 2, M. S. Mount and G. H. Lacy, ed. Academic Press, New York (1982)), which are hereby incorporated by reference). The hypersensitive response elicited by bacteria is readily observed as a tissue collapse if high concentrations ($\geq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199:299–300; Klement, et al., "Hypersensitive Reaction Induced by Phytopathogenic Bacteria in the Tobacco Leaf," *Phytopathology* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in *Phytopathogenic Prokaryotes*, Vol. 2., M. S. Mount and G. H. Lacy, ed. Academic Press, New York (1982), which are hereby incorporated by reference). The capacities to elicit the hypersensitive response in a nonhost and be pathogenic in a host appear linked. As noted by Klement, Z., "Hypersensitivity," pages 149–177 in *Phytopathogenic Prokaryotes*, Vol. 2., M. S. Mount and G. H. Lacy, ed. Academic Press, New York which is incorporated by reference, these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991), which are hereby incorporated by reference). Consequently, the hypersensitive response may hold clues to both the nature of plant defense and the basis for bacterial pathogenicity.

The hrp genes are widespread in gram-negative plant pathogens, where they are clustered, conserved, and in some cases interchangeable (Willis, D. K., et al., "hrp Genes of Phytopathogenic Bateria," *Mol. Plant-Microbe Interact.* 4:132–138 (1991); Bonas, U., "hrp Genes of Phytopathogenic Bacteria," pages 79–98 in: *Current Topics in Microbiology and Immunology: Bacterial Pathogenesis of Plants and Animals—Molecular and Cellular Mechanisms*, J. L. Dangl, ed. Springer-Verlag, Berlin (1994), which are hereby incorporated by reference). Several hrp genes encode components of a protein secretion pathway similar to one used by Yersinia, Shigella, and Salmonella spp. to secrete proteins essential in animal diseases (Van Gijsegem, et al., "Evolutionary Conservation of Pathogenicity Determinants Among Plant and Animal Pathogenic Bacteria," *Trends Microbiol.* 1:175–180 (1993), which is incorporated by reference). In *E. amylovora, P. syringae*, and *P. solanacearum*, hrp genes have been shown to control the production and secretion of glycine-rich, protein elicitors of the hypersensitive response (He, S. Y., et al. "*Pseudomonas Syringae* pv. *Syringae* Harpin$_{Pss}$: a Protein that is Secreted via the Hrp Pathway and Elicits the Hypersensitive Response in Plants," *Cell* 73:1255–1266 (1993), Wei, Z.-H., et al., "HrpI of *Erwinia amylovora* Functions in Secretion of Harpin and is a Member of a New Protein Family," *J. Bacteriol.* 175:7958–7967 (1993); Arlat, M. et al. "PopA1, a Protein Which Induces a Hypersensitive-like Response on Specific Petunia Genotypes, is Secreted via the Hrp Pathway of *Pseudomonas solanacearum*," *EMBO J.* 13:543–553 (1994), which are hereby incorporated by reference).

The first of these proteins was discovered in *E. amylovora* Ea321, a bacterium that causes fire blight of rosaceous plants, and was designated harpin (Wei, Z.-M., et al, "Harpin, Elicitor of the Hypersensitive Response Produced by the Plant Pathogen *Erwinia amylovora*," *Science* 257:85–88 (1992), which is incorporated by reference). Mutations in the encoding hzpN gene revealed that harpin is required for *E. amylovora* to elicit a hypersensitive response in nonhost tobacco leaves and incite disease symptoms in highly susceptible pear fruit. The *P. solanacearum* GMI1000 PopA1 protein has similar physical properties and also elicits the hypersensitive response in leaves of tobacco, which is not a host of that strain (Arlat, et al. "PopA1, a Protein Which Induces a Hypersensitive-like Response on Specific Petunia Genotypes, is Secreted via the Hrp Pathway of *Pseudomonas solanacearum*,"*EMBO J.* 13:543–553 (1994), which is incorporated by reference). However, *P. solanacearum* popA mutants still elicit the hypersensitive response in tobacco and incite disease in tomato. Thus, the role of these glycine-rich hypersensitive response elicitors can vary widely among gram-negative plant pathogens.

*E. chrysanthemi* is unlike the bacterial pathogens that typically elicit the hypersensitive response, because it has a wide host range, rapidly kills and macerates host tissues, and secretes several isozymes of the macerating enzyme pectate lyase (Barras, F., et al., "Extracellular Enzymes and Pathogenesis of Soft-rot Erwinia," *Annu. Rev. Phytopathol.* 32:201–234 (1994), which is incorporated by reference). Nevertheless, pectic enzyme secretion pathway mutants of *E. chrysanthemi* EC16 cause a typical hypersensitive response (Bauer, D. W., et al., "*Erwinia chrysanthemi* hrp Genes and Their Involvement in Soft Rot Pathogenesis and Elicitation of the Hypersensitive Response," *Mol. Plant-Microbe Interact.* 7:573–581 (1994), which is incorporated by reference). Furthermore, elicitation of the hypersensitive response by *E. chrysanthemi* is dependent on a hrp gene that is conserved in *E. amylovora* and *P. syringae* and functions in the secretion of the *E. amylovora* harpin (Wei, Z.-H., et al., "HrpI of *Erwinia amylovora* Functions in Secretion of Harpin and is a Member of a New Protein Family," *J. Bacteriol.* 175:7958– 7967 (1993)i; Bauer, D. W., et al., "*Erwinia chrysanthemi* hap Genes and Their Involvement in Soft Rot Pathogenesis and Elicitation of the Hypersensitive Response," *Mol. Plant-Microbe Interact.* 7:573–581 (1993), which are hereby incorporated by reference).

SUMMARY OF THE INVENTION

The present invention relates to an isolated protein or polypeptide corresponding to a protein or polypeptide in *Erwinia chrysanthemi* which elicits a hypersensitive response in plants. The encoding DNA molecule in isolated form or in either an expression system, a host cell, or a transgenic plant is also disclosed.

Another aspect of the present invention relates to a method of imparting pathogen resistance to plants by transforming them with a DNA molecule encoding the protein or polypeptide capable of eliciting a hypersensitive response in plants and corresponding to a protein or polypeptide in *Erwinia chrysanthemi* which elicits hypersensitive response in plants.

BRIEF DESCRIPTION OF THE DRAWINGS

FIG. 1 shows the DNA sequence of hrpN$_{Ech}$ and predicted amino acid sequence of its product. Underlined are the putative ribosome binding site, the N-terminal amino acids confirmed by sequencing the product of pCPP2172, and a potential rho-independent transcription terminator. The location and orientation of two Tn5-gusA1 insertions are also indicated and are numbered according to their location in the hrpN$_{Ech}$ open reading frame. The accession number for hrpn is L39897.

FIG. 2 compares the predicted amino acid sequences of HrpN$_{Ech}$ and HrpN$_{Ea}$. The predicted amino acid sequences of the *Erwinia chrysanthemi* ("Ech") and *E. amylovora* ("Ea") hrpN products were aligned by the Gap Program of the Genetics Computer Group Sequence Analysis Software Package (Devereaux, J., et al., "A Comprehensive Set of Sequence Analysis Programs for the VAX," *Gene* 12:387–395 (1984)). Two dots denote higher similarity than one dot.

FIG. 4 shows the response of tobacco leaf tissue to purified HrpN$_{Ech}$. Leaf panel 1 was infiltrated with a suspension of purified HrpN$_{Ech}$ at a concentration of 336 μg/ml of 5 mM MES (morpholinoethanesulfonic acid), pH 6.5. Panel 2 was infiltrated with buffer alone. The tissue in panel 1 collapsed 18 hrs. later. The leaf was photographed 24 hrs. after infiltration using a cross-polarized transilluminator, which enhances black and white visualization by making necrotic, desiccated areas that are typical of the hypersensitive response appear black.

FIG. 5 shows a tobacco leaf showing that *Erwinia chrysanthemi* hrpN mutants do not elicit the hypersensitive response unless complemented with hrpN+pCPP2174. Bacteria were suspended at a concentration of 5×10$^8$ cells/ml in 5 mM MES, pH 6.5, and infiltrated into a tobacco leaf. The leaf was photographed 24 hr later using cross-polarized transillumination as in FIG. 4. Panels and strains: 1, *E. chrysanthemi* CUCPB5006 ΔpelABCE); 2, *E. chrysanthemi* CUCPB5045 (ΔpelABCE hrpN$_{Ech}$546::Tn5-gusA1); 3, *E. chrysanthemi* CUCPB5045(pCPP2174); 4, buffer alone; 5, *E. chrysanthemi* CUCPB5046 (ΔpelABCE hrpN$_{Ech}$439:Tn5-gusA1); 6, *E. chrysanthemi* CUCPB5046 (pCPP2174).

FIG. 6A, *E. chrysanthemi* CUCPB5006 ΔpelABCE); FIG. 6B, *E. chrysanthemi* CUCPB5045 (ΔpelABCE hrpN$_{Ech}$546:TnphoA); FIG. 6C, HrpN$_{Ech}$; FIG. 6D, (left side), *E. chrysanthemi* CUCPB5045 (ΔpelABCE hrpN$_{Ech}$546:Tn5-gusA1); 4 (right side), *E. chrysanthemi* CUCPB5063 (ΔpelABCE outD::TnphoA hrpN$_{Ech}$546::Tn5-gusA1).

DETAILED DESCRIPTION OF THE INVENTION AND DRAWINGS

Figure 3:
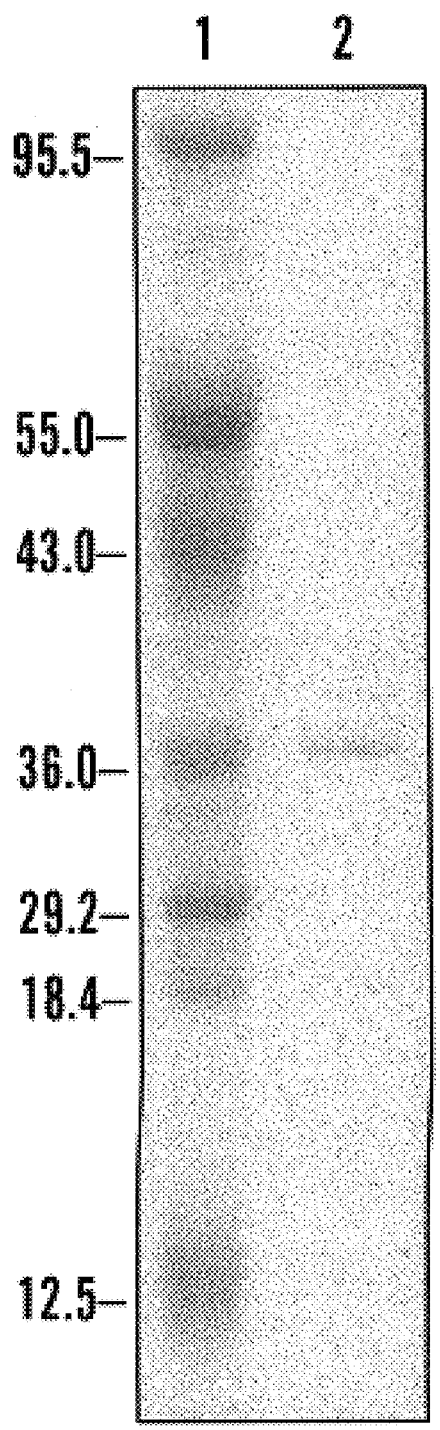
FIG. 3 is an SDS polyacrylamide gel of purified HrpN$_{Ech}$. Purified HrpN$_{Ech}$ was solubilized in SDS loading buffer, electrophoresed through a 12% polyacrylamide gel, and stained with Coomassie Brilliant Blue. Lane 1, molecular weight markers (mid range markers from Diversified Biotech, Boston, Mass.) with size in kD shown to the left; lane 2, HrpN$_{Ech}$.
Figure 6A:
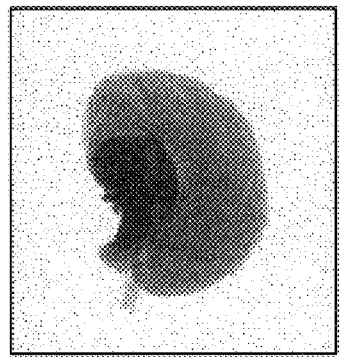
FIGS. 6A–D shows Saintpaulia leaves with rapid necrosis elicited by HrpN$_{Ech}$ and HrpN$_{Ech}$$^+$ Pel-deficient *E. chrysanthemi* strains. Leaves were inoculated with bacteria at a concentration of 3×10$^8$ per milliliter in 5 mM MES, pH 6.5, or purified HrpN$_{Ech}$ at a concentration of 336 μg/ml and photographed 24 hr later as in FIG. 4. Buffer controls elicited no visible response (not shown) Leaves and treatments.
Figure 6B:
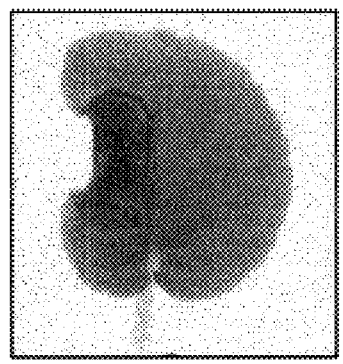
Figure 6C:
Figure 6D:
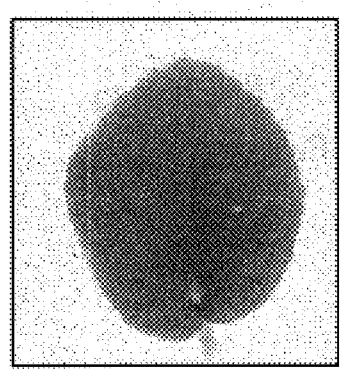

The present invention relates to an isolated DNA molecule encoding for the hypersensitive response elicitor protein or polypeptide from *Erwinia chrysanthemi*. For example, this DNA molecule can comprise the nucleotide sequence corresponding to SEQ. ID. No. 1 as follows:

| | |
|---|---:|
| CGATTTTACC CGGGTGAACG TGCTATGACC GACAGCATCA CGGTATTCGA CACCGTTACG | 60 |
| GCGTTTATGG CCGCGATGAA CCGGCATCAG GCGGCGCGCT GGTCGCCGCA ATCCGGCGTC | 120 |
| GATCTGGTAT TTCAGTTTGG GGACACCGGG CGTGAACTCA TGATGCAGAT TCAGCCGGGG | 180 |
| CAGCAATATC CCGGCATGTT GCGCACGCTG CTCGCTCGTC GTTATCAGCA GGCGGCAGAG | 240 |
| TGCGATGGCT GCCATCTGTG CCTGAACGGC AGCGATGTAT TGATCCTCTG GTGGCCGCTG | 300 |
| CCGTCGGATC CCGGCAGTTA TCCGCAGGTG ATCGAACGTT TGTTTGAACT GGCGGGAATG | 360 |
| ACGTTGCCGT CGCTATCCAT AGCACCGACG GCGCGTCCGC AGACAGGGAA CGGACGCGCC | 420 |
| CGATCATTAA GATAAAGGCG GCTTTTTTTA TTGCAAAACG GTAACGGTGA GGAACCGTTT | 480 |
| CACCGTCGGC GTCACTCAGT AACAAGTATC CATCATGATG CCTACATCGG GATCGGCGTG | 540 |
| GGCATCCGTT GCAGATACTT TTGCGAACAC CTGACATGAA TGAGGAAACG AAATTATGCA | 600 |
| AATTACGATC AAAGCGCACA TCGGCGGTGA TTTGGGCGTC TCCGGTCTGG GGCTGGGTGC | 660 |
| TCAGGGACTG AAAGGACTGA ATTCCGCGGC TTCATCGCTG GGTTCCAGCG TGGATAAACT | 720 |
| GAGCAGCACC ATCGATAAGT TGACCTCCGC GCTGACTTCG ATGATGTTTG GCGGCGCGCT | 780 |
| GGCGCAGGGG CTGGGCGCCA GCTCGAAGGG GCTGGGGATG AGCAATCAAC TGGGCCAGTC | 840 |
| TTTCGGCAAT GGCGCGCAGG GTGCGAGCAA CCTGCTATCC GTACCGAAAT CCGGCGGCGA | 900 |
| TGCGTTGTCA AAAATGTTTG ATAAAGCGCT GGACGATCTG CTGGGTCATG ACACCGTGAC | 960 |
| CAAGCTGACT AACCAGAGCA ACCAACTGGC TAATTCAATG CTGAACGCCA GCCAGATGAC | 1020 |
| CCAGGGTAAT ATGAATGCGT TCGGCAGCGG TGTGAACAAC GCACTGTCGT CCATTCTCGG | 1080 |
| CAACGGTCTC GGCCAGTCGA TGAGTGGCTT CTCTCAGCCT TCTCTGGGGG CAGGCGGCTT | 1140 |
| GCAGGGCCTG AGCGGCGCGG GTGCATTCAA CCAGTTGGGT AATGCCATCG GCATGGGCGT | 1200 |
| GGGGCAGAAT GCTGCGCTGA GTGCGTTGAG TAACGTCAGC ACCCACGTAG ACGGTAACAA | 1260 |
| CCGCCACTTT GTAGATAAAG AAGATCGCGG CATGGCGAAA GAGATCGGCC AGTTTATGGA | 1320 |
| TCAGTATCCG GAAATATTCG GTAAACCGGA ATACCAGAAA GATGGCTGGA GTTCGCCGAA | 1380 |
| GACGGACGAC AAATCCTGGG CTAAAGCGCT GAGTAAACCG GATGATGACG GTATGACCGG | 1440 |
| CGCCAGCATG GACAAATTCC GTCAGGCGAT GGGTATGATC AAAAGCGCGG TGGCGGGTGA | 1500 |
| TACCGGCAAT ACCAACCTGA ACCTGCGTGG CGCGGGCGGT GCATCGCTGG GTATCGATGC | 1560 |
| GGCTGTCGTC GGCGATAAAA TAGCCAACAT GTCGCTGGGT AAGCTGGCCA ACGCCTGATA | 1620 |
| ATCTGTGCTG GCCTGATAAA GCGGAAACGA AAAAAGAGAC GGGGAAGCCT GTCTCTTTTC | 1680 |
| TTATTATGCG GTTTATGCGG TTACCTGGAC CGGTTAATCA TCGTCATCGA TCTGGTACAA | 1740 |
| ACGCACATTT TCCCGTTCAT TCGCGTCGTT ACGCGCCACA ATCGCGATGG CATCTTCCTC | 1800 |
| GTCGCTCAGA TTGCGCGGCT GATGGGGAAC GCCGGGTGGA ATATAGAGAA ACTCGCCGGC | 1860 |
| CAGATGGAGA CACGTCTGCG ATAAATCTGT GCCGTAACGT GTTTCTATCC GCCCCTTTAG | 1920 |
| CAGATAGATT GCGGTTTCGT AATCAACATG GTAATGCGGT TCCGCCTGTG CGCCGGCCGG | 1980 |
| GATCACCACA ATATTCATAG AAAGCTGTCT TGCACCTACC GTATCGCGGG AGATACCGAC | 2040 |
| AAAATAGGGC AGTTTTTGCG TGGTATCCGT GGGGTGTTCC GGCCTGACAA TCTTGAGTTG | 2100 |
| GTTCGTCATC ATCTTTCTCC ATCTGGGCGA CCTGATCGGT T | 2141 |

Also encompassed by the present invention are fragments of the DNA molecule comprising the nucleotide sequence corresponding to SEQ. ID. No. 1. Suitable fragments capable of eliciting the hypersensitive response (i.e. eliciting necrosis in plants) are constructed by using appropriate restriction sites, revealed by inspection of the DNA molecule's sequence, to: (i) insert an interposon (Felley, et al., "Interposon Mutagenesis of Soil and Water Bacteria: a Family of DNA Fragments Designed for in vitro Insertion Mutagenesis of Gram-negative Bacteria, *Gene* 52:147–15 (1987), which is hereby incorporated by reference) such that truncated forms of the hypersensitive response elicitor polypeptide or protein, that lack various amounts of the C-terminus, can be produced or (ii) delete various internal portions of the protein. Alternatively, the sequence can be used to amplify any portion of the coding region, such that it can be cloned into a vector supplying both transcription and translation start signals.

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide.

The DNA molecule, corresponding to SEQ. ID. No. 1, contains an open reading frame which codes for the hypersensitive response elicitor polypeptide or protein from *Erwinia chrysanthemi* and corresponds to SEQ. ID. No. 2 as follows:

```
Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285

Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

This protein or polypeptide has a molecular weight of 32 to 36 kDa, preferably 34 kDa. It is heat stable (i.e., activity is retained upon boiling for 10 min.), has a glycine content of greater than 16%, and contains no cysteine.

The DNA molecule containing just the open reading frame coding for SEQ. ID. No. 2 has the nucleotide sequence corresponding to SEQ. ID. NO. 6 as follows:

tures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11,

| 1 | ATGCAAATTACGATCAAAGCGCACATCGGCGGTGATTTGGGCGTCTCCGGTCTGGGGCTG | 60 |
|---|---|---|
| 61 | GGTGCTCAGGGACTGAAAGGACTGAATTCCGCGGCTTCATCGCTGGGTTCCAGCGTGGAT | 120 |
| 121 | AAACTGAGCAGCACCATCGATAAGTTGACCTCCGCGCTGACTTCGATGATGTTTGGCGGC | 180 |
| 181 | GCGCTGGCGCAGGGGCTGGGCGCCAGCTCGAAGGGGCTGGGGATGAGCAATCAACTGGGC | 240 |
| 241 | CAGTCTTTCGGCAATGGCGCGCAGGGTGCGAGCAACCTGCTATCCGTACCGAAATCCGGC | 300 |
| 301 | GGCGATGCGTTGTCAAAAATGTTTGATAAAGCGCTGGACGATCTGCTGGGTCATGACACC | 360 |
| 361 | GTGACCAAGCTGACTAACCAGAGCAACCAACTGGCTAATTCAATGCTGAACGCCAGCCAG | 420 |
| 421 | ATGACCCAGGGTAATATGAATGCGTTCGGCAGCGGTGTGAACAACGCACTGTCGTCCATT | 480 |
| 481 | CTCGGCAACGGTCTCGGCCAGTCGATGAGTGGCTTCTCTCAGCCTTCTCTGGGGCAGGC | 540 |
| 541 | GGCTTGCAGGGCCTGAGCGGCGCGGGTGCATTCAACCAGTTGGGTAATGCCATCGGCATG | 600 |
| 601 | GGCGTGGGGCAGAATGCTGCGCTGAGTGCGTTGAGTAACGTCAGCACCCACGTAGACGGT | 660 |
| 661 | AACAACCGCCACTTTGTAGATAAAGAAGATCGCGGCATGGCGAAAGAGATCGGCCAGTTT | 720 |
| 721 | ATGGATCAGTATCCGGAAATATTCGGTAAACCGGAATACCAGAAAGATGGCTGGAGTTCG | 780 |
| 781 | CCGAAGACGGACGACAAATCCTGGGCTAAAGCGCTGAGTAAACCGGATGATGACGGTATG | 840 |
| 841 | ACCGGCGCCAGCATGGACAAATTCCGTCAGGCGATGGGTATGATCAAAAGCGCGGTGGCG | 900 |
| 901 | GGTGATACCGGCAATACCAACCTGAACCTGCGTGGCGCGGGCGGTGCATCGCTGGGTATC | 960 |
| 961 | GATGCGGCTGTCGTCGGCGATAAAATAGCCAACATGTCGCTGGGTAAGCTGGCCAACGCC | 1020 |
| 1021 | TGA | 1023 |

The protein or polypeptide of the present invention is preferably produced in purified form (preferably, at least: about 80%, more preferably 90%, pure) by conventional techniques. Typically, the protein or polypeptide of the present invention is isolated from E. coli by lysing and sonication. After washing, the lysate pellet is resuspended in buffer containing Tris-HCl. During dialysis, a precipitate forms from this protein solution. The solution is centrifuged, and the pellet is washed and resuspended in the buffer containing Tris-HCl. Proteins are resolved by electrophoresis through an SDS 12% polyacrylamide gel.

The DNA molecule C encoding the hypersensitive response elicitor polypeptide from Erwinia chrysanthemi can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

gt WES.tB, Charon 4, and plasmid vectors such as pER322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La. Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes MRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic: cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the MRNA. This sequence is a short nucleotide sequence of MRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promotors may be used. For instance, when cloning in *E. coli*, its bacteriophages, or plasmids, promoters such as the T7 phage promoter, lac promotor, trp promotor, reca promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequences about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor protein or polypeptide from *Erwinia chrysanthemi* has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

One aspect of the present invention involves using the DNA molecule encoding the hypersensitive response elicitor from *Erwinia chrysanthemi* to transform plants in order to impart localized resistance to pathogens, such as bacteria, fungi, nematodes, and viruses, using a promoter specifically activated by one or more of these pathogens. As a result, when the transgenic plant is infiltrated by such pathogens, the leaves of the plant will undergo localized collapse. This confines the pathogen so that further growth is prevented, and, ultimately, the pathogen perishes. Transformation of plants with the DNA molecule of the present invention is particularly useful where the plant does not exhibit a hypersensitive response to pathogens or is weakly responsive to such pathogens. This requires that $hrpN_{ech}$ be hooked up to the promotor of a plant gene that the pathogen induces such as PAL, CHS, etc. Otherwise, hrpN will kill the plant. It may also be appropriate to transform plants with this DNA molecule where the pathogens they are susceptible to do not elicit a hypersensitive response or elicit a response which is weak.

This aspect of the present invention requires that the subject DNA molecule be incorporated in plants with a suitable promoter which is activated by pathogen infection. Suitable promoters for these purposes include those from the following genes: genes expressed in response to fungus and bacterial infection (e.g., genes encoding phenylalanine ammonia lyase and chalcone synthase) and genes involved in the development of senescence.

The isolated DNA molecule of the present invention can be utilized to impart localized resistance to pathogens for a wide variety of plants, including both monocots and dicots. Although the gene can be inserted into any plant falling within these broad classes, it is particularly useful in crop plants, such as rice, wheat, barley, rye, corn, potato, sweet potato, bean, pea, chicory, lettuce, endive, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane. The present invention may also be used in conjunction with non-crop plants, including *Arabidopsis thaliana*, saintpaulia, petunia, pelargonium, and zinnia.

The expression system of the present invention can also be used to transform virtually any plant cell under suitable conditions. Cells transformed in accordance with the present invention can be grown in vitro in a suitable medium to impart localized resistance to pathogens. Transformed cells can be regenerated into whole plants such that this protein imparts localized resistance to pathogens to the intact transgenic plants. In either case, the plant cells transformed with the recombinant DNA expression system of the present invention are grown and caused to express that DNA in the cells in response to a pathogen to impart localized resistance to pathogens on them.

One technique of transforming plants with the DNA molecule in accordance with the present invention is by contacting the tissue of such plants with an inoculum of a bacteria transformed with a vector comprising a gene in accordance with the present invention which imparts localized resistance to pathogens. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized to transform plant cells. Suitable species of such bacterium include *Agrobacterium tumefaciens* and *Agrobacterium rhizogenes*. *Agrobacterium tumefaciens* (e.g., strains LBA4404 or EHA105) is particularly useful due to its well-known ability to transform plants.

Another approach to transforming plant cells with a gene which imparts localized resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

The hypersensitive response elicitor polypeptide or protein of the present invention can be applied to all or part of the plants listed previously to impart resistance to the plants. In this procedure, the polypeptide or protein alone, mixed with a carrier, and/or with plant treating agents (e.g., fertilizers, insecticides, fungicides, etc.) can be applied to plant. Such application requires infiltration of the polypeptide or protein into the plant by, for example, injection, leaf abrasion proximate to the time of application, or high pressure spraying.

The isolated DNA molecule of the present invention could be used to generate male sterile plants used in plant breeding for generation of hybrids. A promoter from a plant gene involved specifically in pollen development could be useds to express the hypersensitive response elicitor polypeptide or protein in anthers, resulting in death of the anther and/or pollen.

The hypersensitive response elicitor polypeptide or protein of the present invention could be used as a regulatable suicide factor to kill a transgenic plant on demand. If it were engineered to be expressed from a promoter that is induced in response to a normally nontoxic, environmentally friendly, inducer molecule, the plant could be killed by spraying with the inducer molecule rather than with herbicides. This could be used, for example, instead of herbicides to kill potato vines to facilitate harvest and reduce the devastating tuber blight phase of late blight. This could also be linked with other transgenes to permit the control of a transgenic plant that escaped or outcrossed with a weed. For example, a concern with pathogen-derived resistance to viruses is that the virus resistance genes could spread from the transgenic crop to related weeds that are normally held in check by natural virus infections. These new, more hardy weeds, would now be sensitive to killing by the inducer of the gene.

The hypersensitive response elicitor polypeptide or protein of the present invention may be used as a selective herbicide in synergistic combination with an avirulence protein that interacts with a resistance gene product that is unique t:-o the targeted weed (or is lacking from crop plants).

It may be possible to use the hypersensitive response elicitor polypeptide or protein of the present invention in a tissue culture selection scheme to select cultures that are resistant to it. Regenerated plants may then be resistant to *E. chrysanthermi* and may even be resistant to a wide range of plant pathogenic bacteria. It is possible that this protein or polypeptide has effects on animal cells that could be exploited for medical use, insect control.

The hypersensitive response elicitor protein or polypeptide can also be used to raise monoclonal or polyclonal antibodies by conventional procedures. At least the binding portions of these antibodies can be sequenced and encoding DNA synthesized. The encoding DNA molecule can be used to transform plants together with a promoter which causes expression of the encoded protein when the plant is infected by *Erwinia chrysanthemi*. The expressed protein will bind to the pathogen and help prevent the usual necrotic response. Antibodies to this protein or polypeptide of the present invention could also be used to identify pathogenic Erwinia.

EXAMPLES

Example 1

Bacterial Strains, Plasmids and Culture Conditions

Bacterial strains and plasmids are listed in Table 1.

TABLE 1

Bacterial strains and plasmids utilized

| Designation | Relevant characteristics[a] | Reference or source |
|---|---|---|
| *Escherichia coli* ED8767 | supE44 supF58 hsdS3 ($r_B^-$ $m_B^-$) recA56 galK2 galT22 metB1 | (Sambrook et al. 1989)[b] |
| DH5α | supE44 ΔlacU169 (φ80 lacZΔM15) hsdR17 recA1 endA1 gyrA95 thi-1 relA1 Nal$^r$ | (Hanahan 1983)[c]; Life Technologies, Inc. (Grand Island, NY) |
| DH10B | mcrA Δ(mrr-hsdRMS-mcrBC) φ80 lacZΔM15 ΔlacX74 deoR recA1 endA1 araD139 Δ(ara, leu) 7697 galU galK rpsL nupG | (Grant et al. 1990)[d]; Life Technologies, Inc. |
| *Erwinia chrysanthemi* EC16 | Wild-type strain | (Burkholder et al. 1953)[e] |
| AC4150 | Spontaneous Nal$^r$ derivative of EC16 | (Chatterjee et al. 1983)[f] |
| CUCPB5006 | Δ(pelB peC)::28bp Δ(pelA pelE) derivative of AC4150 | (He and Collmer 1990)[g] |
| CUCPB5030 | outD::TnphoA derivative | (Bauer et al. |

TABLE 1-continued

Bacterial strains and plasmids utilized

Figure 7:
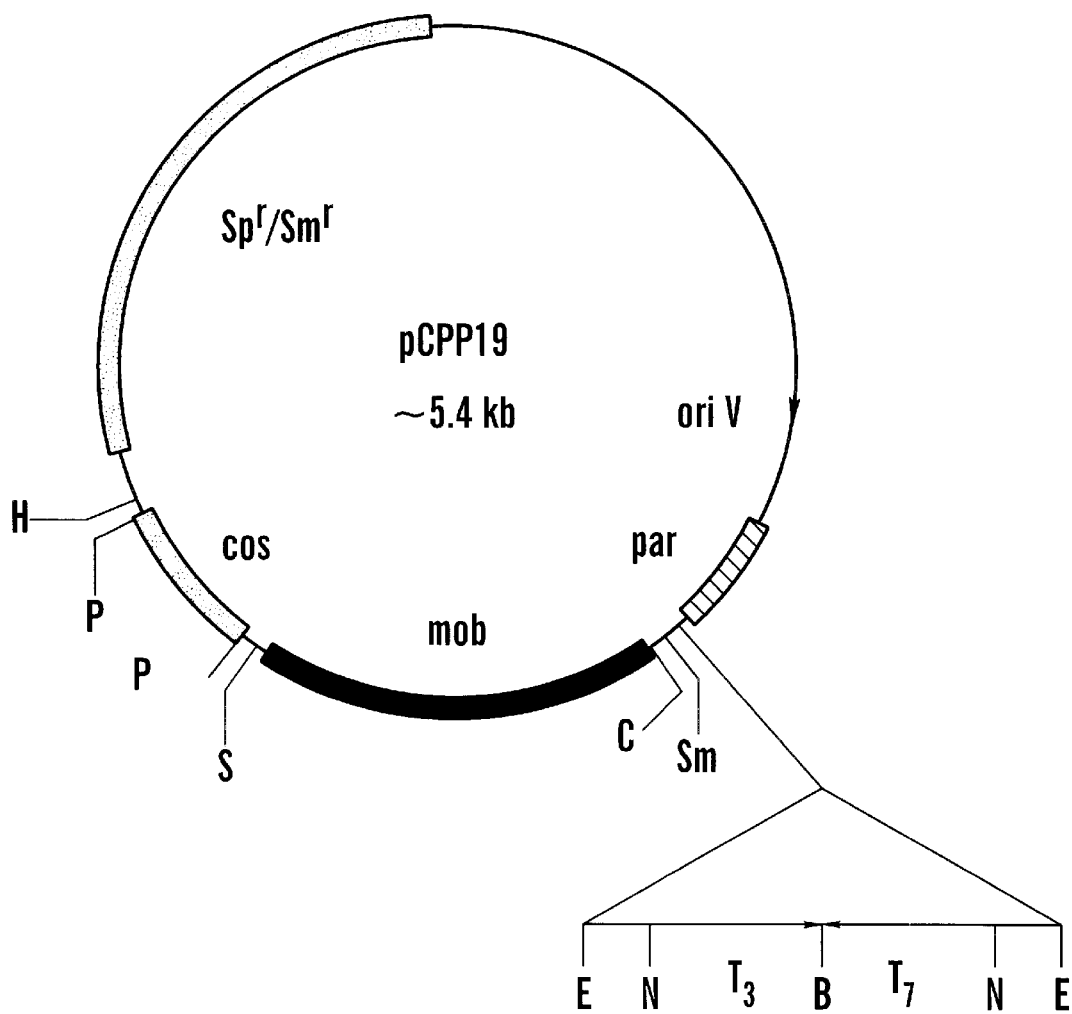
FIG. 7 shows a diagram of plasmid pCPP19. Significant features are the mobilization (mob) site for conjugation; the cohesive site of λ (cos); and the partition region (par) for stable inheritance of the plasmid. B, BamHI; E, EcoRI; H, HindIII; N, NotI; P, PstI; S. SalI; Sm, SmaI; T3, bacteriophage T3 promoter; T7, bacteriophage T7 promoter; oriV, origin of replication; Sp$^r$, spectinomycin resistance; Sm$^r$, streptomycin resistance.

| Designation | Relevant characteristics[a] | Reference or source |
|---|---|---|
| | of CUCPB5006 | 1994)[h] |
| CUCPB5045 | hrpN$_{Ech}$546::Tn5-gusA1 derivative of CUCPB5006 | Described in this application |
| CUCPB5046 | hrpN$_{Ech}$439::Tn5-gusA1 derivative of CUCPB5006 | Described in this application |
| CUCPB5063 | hrpN$_{Ech}$546::Tn5-gusA1 derivative of CUCPB5030 | Described in this application |
| CUCPB5049 | hrpN$_{Ech}$:439::Tn5-gusA1 derivative of AC4150⁺ | Described in this application |
| *Erwinia amylovora* | | |
| Ea321 | Wild type | ATCC 49947; CNPB 1367 |
| Ea321T5 | hrpN$_{Ea}$::Tn5tac1 derivative of Ea321 | (Wei et al. 1992)[i] |
| Plasmids and phage | | |
| pBluescript II SK(−) | Amp$^r$ | Stratagene (La Jolla CA) |
| pCCP19 | Cosmid Vector, Sp$^r$/Sm$^r$ | See FIG. 7. |
| pUC119 | Amp$^r$ plasmid vector | (Vieira and Messing 1987)[j] |
| pSE280 | Amp$^r$ plasmid vector with superpolylinker downstream of tac promoter | (Brosius 1989)[k] |
| pCPP2030 | pCPP19 carrying *E. chrysanthemi* DNA hybridizing with *E. amylovora* hrp genes in pCPP1033 | (Bauer et al. 1994)[h] |
| pCPP1084 | pBluescript M13+ carrying hrpN$_{Ea}$ on 1.3 kb HindIII fragment | (Wei et al. 1992)[i] |
| pCPP2157 | pCPP19 carrying *E. chrysanthemi* DNA hybridizing with *E. amylovora* hrpN | Described in this application |
| pCPP2142 | 8.3 kb SalI subclone from pCPP2157 in pUC119 | Described in this application |
| pCPP2141 | 3.1 kb PstI subclone from pCPP2157 in pBluescript II SK(−) hrpN$_{Ech}$ in opposite orientation from vector lac promoter | Described in this application |
| pCPP2172 | 3.1 kb PstI subclone from pCPP2157 in pBluescript II SK(−) hrpN$_{Ech}$ in same orientation as vector lac promoter | Described in this application |
| pCPP2174 | 1.0 kb hrpN$_{Ech}$ + PCR product cloned in NcoI-HindIII sites of pSE280 | Described in this application |
| λ::Tn5-gusA1 | Tn5 derivative for generating transcriptional fusions with uidA receptor; Kan$^r$, Tet$^r$ | (Sharma and Signer 1990)[l] |

[a]Amp$^r$ = ampicillin resistance: Nal$^r$ = nalidixic acid resistance; Sm$^r$ = streptomycin resistance; Sp$^r$ = spectinomycin resistance; Tet$^r$ = tetracycline resistance
[b]Sambrook, J., Fritsch, E. F., and Maniatis, T., Molecular Cloning. A laboratory Manual, Second Edition. Cold Spring Harbor, Cold Spring Harbor (1989), which is hereby incorporated by reference.
[c]Hanahan, D., "Studies on Transformation of *Escherichia coli* with Plasmids," J. Mol. Biol. 166: 557–580 (1983), which is hereby incorporated by reference.
[d]Grant, S. G. N., Jessee, J., Bloom, F. R., and Hanahan, D., "Differential Plasmid, Rescue from Transgenic Mouse DNAs in *Escherichia coli* Methylation-restriction Mutants," Proc. Nat. Acad. Sci. U.S.A. 87465–46949 (1990), which is hereby incorporated by reference.
[e]Burkholder, W, H., McFadden, L. A., and Dimock, A. W, "A Bacterial Blight of Chrysanthemums," Phytopathology 43: 522–526 (1953), which is hereby incorporated by reference.
[f]Chatterjee, A. K., Thurn, K. K., and Feese, D. A." Tn5 Induced Mutations in the Enterobacterial Phytopathogen *Erwinia chrysanthemi*," Appl. Environ. Microbiol. 45: 644–650 (1983), which is hereby incorporated by reference.
[g]He, S. Y., and Collmer, A, "Molecular Cloning, Nucleotide Sequence and Marker-exchange Mutagenesis of the Exo-poly-α-D-galacturonosidase-encoding pehX Gene of *Erwinia chrysanthemi* EC16," J. Bacteriol. 172: 4988–4995 (1990), which is hereby incorporated by reference.
[h]Bauer, D. W., Bogdanove, A. J., Beer, S. V., and Collmer, A., "Erwinia Chrysanthemi hrp Genes and their Involvement in Soft Rot Pathogenesis and Elicitation of the Hypersensitive Response," Mol. Plant-Microbe Interact., 7: 573–581 (1994), which is hereby incorporated by reference.
[i]Wei, Z. -M., Laby, R. J., Zumoff, C. H., Bauer, D. W., He, S. Y., Collmer, A., and Beer, S. V., "Harpin, Elicitor of the Hypersensitive Response Produced by the Plant Pathogen *Erwinia amylovora*," Science 257: 85–88 (1992), which is hereby incorporated by reference.
[j]Vieira, J., and Messing, J., "Production of Single-stranded Plasmid DNA," Meth. Enzymol. 153: 3–11 (1987), which is hereby incorporated by reference.
[k]Brocius, J., "Superpolylinkers in Cloning and Expression Vectors," DNA 8: 759–777 (1989), which is hereby incorporated by reference.
[l]Sharma, S. B., and Signer, E. R., "Temporal and Spatial Regulation of the Symbiotic Genes of *Rhizobium meliloti* in Planta Revealed by Transposon Tn5-gusA," Genes Develop. 4: 344–356 (1990), which is hereby incorporated by reference.

*E. chrysanthemi* was routinely grown in King's medium B ("KB") (King, E. O. et al., "Two Simple Media for the Demonstration of Pyocyanin and Fluorescein," J. Lab. Med. 22:301–307 (1954), which is hereby incorporated by reference) at 30° C., *E. coli* in LM medium (Hanahan, D., "Studies on transformation of *Escherichia coli* with Plasmids," J. Mol. Biol. 166:557–580 (1983), which is incorporated by reference) at 37° C., and *E. amylovora* in LB medium at 28–30° C. The following antibiotics were used in selective media in the amounts indicated (µg/ml) except where noted: ampicillin, 100; kanamycin, 50; spectinomycin, 50; and streptomycin, 25.

Example 2

General DNA Manipulations

Plasmid DNA manipulations, colony blotting, and Southern blot analyses were performed using standard techniques (Sambrook, J., et al., "Molecular Cloning. A Laboratory Manual," Second Edition, *Cold Spring Harbor*, Cold Spring Harbor (1989), which is incorporated by reference). Deletions for sequencing were constructed with the Erase-a-Base Kit (Promegsa, Madison, Wis.). Double stranded DNA sequencing templates were prepared using Qiagen Plasmid Mini Kits (Chatsworth, Calif.). Sequencing was performed using the Sequenase Version 2 kit (U.S. Biochemical, Cleveland, Ohio). The Tn5-gusA1 insertion points were determined on an Applied Biosystems (Foster City, Calif.) Automated DNA Sequencer Model 373A by the Cornell Biotechnology Center. DNA sequences were analyzed with the Genetics Computer Group Sequence Analysis Software Package (Devereaux, J., et al., "A Comprehensive Set of Sequence Analysis Programs for the VAX," Gene 12:387–395 (1984), which. is hereby incorporated by reference). Comparison of HrpN$_{Ech}$ (i.e. the gene encoding the hypersensitive response elicitor polypeptide or protein from *Erwinia chrysanthemi*) and HrpN$_{Ea}$ (i.e. the gene encoding the hypersensitive response elicitor polypeptide or protein from Erwinia amylovora) by the Gap Program was done with a gap weight of 5.0 and a gap length weight of 0.3. Marker-exchange mutagenesis was performed as described (Bauer, D. W., et al., "*Erwinia chrysanthemi* hzp Genes and Their Involvement in Soft Rot Pathogenesis and Elicitation of the Hypersensitive Response," *Mol. Plant-Microbe Interact,* 7:573–581 (1994), which is incorporated by reference). The oligonucleotide used to determine the location of Tn5-gusA1 insertions in hrp$N_{Ech}$ was TGACCTGCAGCCAAGCTTTCC (SEQ. ID. No. 3). The oligonucleotide used as the first primer to amplify the hrp$N_{Ech}$ ORF and to introduce a Ncol site at the 5' end of the gene was AGTACCATGGTTATTACGATCAAAGCGCAC (SEQ. ID. No. 4); the one used as the second primer to introduce an Xhol site at the 3' end of the gene was AGATCTCGAGGGCGTTGGCCAGCTTl(CC (SEQ. ID. No. 5). Primers were synthesized by Integrated DNZI Technologies (Coralville, Iowa).

Example 3

Protein Manipulations

Hrp$N_{Ech}$ was purified from *E. coli* Dh5α(pCPP2172) cultures grown at 30° C. to stationary phase in 50 ml of Terrific Broth (Sambrook, J., et al., "Molecular Cloning. A Laboratory Manual," Second Edition, *Cold Spring Harbor*, Cold Spring Harbor (1989), which is incorporated by reference) supplemented withl ampicillin at a concentration of 200μg/ml. fells were lysed by lysozyme treatment and sonication as described (Sambrook J., et al., "Molecular Cloning. A Laboratory Manual," Second Edition, *Cold Spring Harbor*, Cold Spring Harbor (1989), which is incorporated by reference). The lysate pellet was washed twice with 9 volumes of lysis buffer containing 0.5% Triton X-100 and 10 mM EDTA, pH 8.0, 0.1 mM phenylmethylsulfonyl fluoride (PMSF), and reharvested each time by centrifugation at 12,000× g for 15 min. The pellet was resuspended in 2.0 ml lysis buffer containing 0.1 mM PMSF, dissolved by the addition of 2.5 ml of 8 M guanidine-HCl in lysis buffer and then diluted with 5.0 ml water. The protein solution was dialyzed in SpectraPor #1 dialysis tubing against 2.0 I of 5 mM MES, pH 6.5, containing 0.05 mM PMSF. The precipitate that formed during dialysis and the solution were centrifuged for 15 min at 4,300× g. The pellet was washed once with 10 ml of 5 mM MES, pH. 6.5, with 0.1 mM PMSF and then resuspended in 2.0 ml of the same buffer. Protein concentrations of homogeneous suspensions were determined following dissolution in the reagents of the dye-binding assay of Bradford (Bradford, M., "A Rapid and Sensitive Method for the Quantitation of Microgram Quantities of Protein Utilizing the Principle of Protein-dye-binding," *Anal. Biochem,* 92:248–2254 (1976), which is incorporated by reference). Proteins in crude cell lysates or following purification were resolved by electrophoresis through an SDS 120 polyacrylamide gel and visualized by staining with Coomassie Brilliant Blue R. The N-terminal sequence of purified Hrp$N_{Ech}$ was determined at the Cornell University Biotechnology Program Analysis Facility.

Example 4

Plant Assays

Tobacco (*Nicotiana tabacum L.* var *Xanthi*), tomato (*Lycopersicon esculentum Mill.* var *Sweet* 199), pepper (*Capsicum annuum L.* var *Sweet Hungarian*), Saintpaulia (*S. ionantha Wendl.* var. *Paris*), petunia (*P. grandiflora Juss.* var. *Blue Frost*), pelargonium (*P. hortorum Bailey*), winter squash (*Cucurbita maxima Duchesne.*), and Zinnia (*Z. elegans Jacq.*) plants were grown under greenhouse conditions or purchased at a local garden shop and then maintained in the laboratory at room temperature, with incident daylight supplemented with a 500 W halogen lamp, for hypersensitive response assays. Witloof chicory (*Cichorium intybus L.*) "IBelgian endive" heads were purchased from a local supermarket. Bacterial inoculum was prepared and delivered as previously described (Bauer, D. W., et al., "*Erwinia chrysanthemi* hrp Genes and Their Involvement in S Soft Rot Pathogenesis and Elicitation of the Hypersensitive Response," *Mol. Plant-Microbe Interact,* 7:573–581 (1994) which is incorporated by reference). Briefly, to assay soft-rot pathogenesis, 5 μl of inoculum was applied to a small wound in detached chicory leaves; to assay for hypersensitive response elicitation, inoculum was injected into the intercellular spaces of plant leaves with a needle-less plastic syringe. Hereafter, in these examples, this injection procedure is referred to as "infiltrated" or as "infiltration".

Example 5

Molecular Cloning of the *E. chrysanthemi* hrp$N_{Ech}$ Gene

Eighteen cosmids containing *E. chrysanthemi* DNA sequences hybridizing with a region of the *E. amylovora* hrp cluster that is widely conserved in plant pathogenic bacteria. were previously isolated (Bauer, D. W., et al., "*Erwinia chrysanthemi* hrp Genes and Their Involvement in Soft Rot Pathogenesis and Elicitation of the Hypersensitive Response," *Mol. Plant-Microbe Interact,* 7:573–581 (1994), which is incorporated by reference). The pattern of restriction fragments released from these cosmids indicated they all contained overlapping inserts from the same region of the *E. chrysanthemi* genome. The cosmids were probed in colony blots with a 1.3 kb Hindlll fragment from pCPP1084, which contains the *E. amylovora* hrpN gene (Wei, Z.-M., et al., "Harpin Elicitor of the Hypersensitive Response Produced by the Plant: Pathogen," *Science* 257:85–88 (1992), which is incorporated by reference). pCPP2157, one of the three cosmids hybridizing with the probe, was digested with several restriction enzymes, and the location of the hrp$N_{Ech}$ gene in those fragments was determined by probing a Southern blot with the *E. amylovora* Hindlll fragment. Two fragments, each containing the entire hrp$N_{Ech}$ gene, were subcloned into different vectors: pCPP2142 contained an 8.3 kb SalI fragment in pUC119 (Vieira, J., et al., "Production of Single-stranded Plasmid DNA, *Meth. Enzymo,* 153:3–11 (1987), which is incorporated by reference), and pCPP2141 contained a 3.1 kb Pstl fragment in pBluescript II SK(−) (Stratagene, La Jolla, Calif.) and was used to sequence the hrp$N_{Ech}$ gene.

Example 6

Sequence of hrp$N_{Ech}$

The nucleotide sequence of a 2.4 kb region of pCPP2141 encompassing hrp$N_{Ech}$ was determined. The portion of that sequence extending from the putative ribosome binding site through the hrp$N_{Ech}$ coding sequence to a putative rho-independent terminator is presented in FIG. 1. The typical ribosome-binding site, consisting of GAGGA, was located 10 bases upstream of the ATG translational initiation codon. No promoter sequences were discernible upstream of hrp-$N_{Ech}$. Instead, the presence of another open reading frame suggested that hrp$N_{Ech}$ is the last open reading frame in a polycistronic operon. hrpN$_{Ech}$ codes for a predicted protein that is 34.3 kD, rich in glycine (16.2%) and lacking in cysteine. Comparison of the amino acid sequences of the predicted hrpN$_{Ea}$ and hrpN$_{Ech}$ products revealed extensive similarity, particularly in the C-terminal halves of the proteins (FIG. 2). The overall identity of the hrpN genes and proteins was 66.9% and 45.5%, as determined by the FASTA and Gap algorithms, respectively (Devereaux, J., et al., "A Comprehensive Set of Sequence Analysis Programs for the VAX," *Gene* 12:387–395 (1984); Pearson, W. R., et al., "Improved Tools for Biological Sequence Comparison," *Proc. Natl. Acad. Sci. U.S.A.,* 85:2444–2448 (1988), which are hereby incorporated by reference).

The direction of hrpN$_{Ech}$ transcription, the size of the predicted product, and the translation start site were confirmed by recloning the 3.1 kb PstI fragment from pCPP2157 and selecting a clone with the fragment in pbluescript II SK(−) in the opposite orientation from pCPP2141 to produce pCPP2172. *E. coli* DH5α(pCPP2172) expressed hrp-N$_{Ech}$ from the vector lac promoter and produced high levels of a protein with an estimated molecular mass of 36 kD in SDS polyacrylamide gels, which is close to the predicted size (FIG. 3). Furthermore, the N-terminal 10 amino acids of the 36 kD protein, determined by microsequencing following purification as described below, corresponded with the predicted N-terminus of HrpN$_{Ech}$. No N-terminal signal sequence for targeting to the general export (Sec) pathway was discernible in the HrpN$_{Ech}$ sequence, and the data showed no evidence of processing of the N-terminus.

Example 7

Purification of the hrpN$_{Ech}$ Product and Demonstration of its Hypersensitive Response Elicitor Activity in Tobacco When DH5α(pCPP2172) cells were disrupted by sonication and then centrifuged, most of the HrpN$_{Ech}$ protein sedimented with the cell debris. However, soluble HrpN$_{Ech}$ could be released from this material by treatment with 4.5 M guanidine-HCl. This suggested that the protein formed inclusion bodies which could be exploited for purification. As detailed in Example 3, it was found that HrpN$_{Ech}$ reprecipitated when the guanidine-HCl was removed by dialysis against dilute buffer. The HrpN$_{Ech}$ precipitate could be washed and resuspended in buffer, in which it formed a fine suspension. SDS polyacrylamide gel analysis revealed the suspension to be electrophoretically homogeneous Hrp-N$_{Ech}$ (FIG. 3).

Cell-free lysates from *E. coli* DH5α(pCPP2172) cells grown in LB medium were infiltrated into tobacco leaves. Necrosis typical of the hypersensitive response developed within 18 hr, whereas leaf panels infiltrated with identically prepared lysates of DH5α(pBluescript SK-) showed no response. The suspension of purified HrpN$_{Ech}$ at a concentration of 336 jig/ml also caused a necrotic response within 18 hrs. that was indistinguishable from that caused by *E. chrysanthemi* CUCBP5030 or cell-free lysates from *E. coli* DH5α(pCPP2172) (FIG. 4). Tobacco plants vary in their sensitivity to harpins, and elicitation of the hypersensitive response by HrpN$_{Ech}$ at lower concentrations was found to be variable. Consequently, a concentration of 336 µg/ml was used in all subsequent experiments. The concentration of HrpN$_{Ech}$ that is soluble in apoplastic fluids is unknown. To determine the heat stability of HrpN$_{Ech}$, the suspension of purified protein was incubated at 100° C. for 15 min and then infiltrated into a tobacco leaf. There was no apparent diminution in its ability to elicit the hypersensitive response. These observations indicated that HrpN$_{Ech}$ is sufficient to account for the ability of *E. chrysanthemi* to elicit the hypersensitive response in tobacco.

Example 8 hrpN$_{Ech}$ Mutants Fail to Elicit the Hypersensitive response in Tobacco

*E. coli* DH10B(pCPP2142) was mutagenized with Tn5-gusA1 (Sharma, S. B., et al., "Temporal and Spatial Regulation of the Symbiotic Genes of *Rhizobium meliloti* in Planta Revealed by Transposon TN5-gusA, *Genes Develop* 4:344–356 (1990), which is incorporated by reference). Plasmid DNA was isolated from kanamycin-resistant colonies and transformed into *E. coli* DH5S, with selection for kanamycin resistance. Plasmids containing Tn5-gusA1 were analyzed by restriction mapping. Two independent insertions in an 0.82 kb ClaI fragment internal to hrpN$_{Ech}$ were chosen for further study. The precise location and orientation of these insertions was determined by using a primer that hybridizes to Tn5-gusA1 DNA upstream of gusA to sequence into the disrupted *E. chrysanthemi* DNA (FIG. 1). *E. coli* DH5α(pCPP2142) cells carrying the Tn5-gusA1 insertion at nucleotide 439 of the hrpN$_{Ech}$ open reading frame (with gusA and hrpN$_{Ech}$ in the same orientation) produced dark blue colonies indicative of β-glucuronidase activity on LM agar supplemented with 5-bromo-4-chloro-3-indolyl β-D-glucuronide. Whether gusA was expressed from an *E. chrysanthemi* promoter or the vector lac promoter was not determined. The hrpN$_{Ech}$439::Tn5-gusA1 and hrpN$_{Ech}$546::Tn5-gusA1 mutations were marker-exchanged into the genome of *E. chrysanthemi* CUCPB5006 (ΔpelABCE) to produce mutants CUCPB5046 and CUCPB5045, respectively. Neither of the hrpN$_{Ech}$ mutants elicited a visible reaction in tobacco leaves (FIG. 5.)

Example 9

*E. chrysanthemi* hrpN$_{Ech}$ Mutations can be Complemented in trans with hrpN$_{Ech}$ but not with hrpN$_{Ea}$ The presence of a typical rho-independent terminator just downstream of the hrpN$_{Ech}$ open reading frame suggested that mutations in the gene would not have polar effects on any other genes and that the hypersensitive response elicitation phenotype should be restored by a hrpN$_{Ech}$ subclone. Because pCPP2172 carried 2 kb of *E. chrysanthemi* DNA in addition to hrpN$_{Ech}$, a precise subclone of the gene was constructed for this purpose. Oligonucleotides were used to PCR-amplify the hrpN$_{Ech}$ open reading frame and to introduce terminal NcoI and XhoI sites. The introduction of the restriction sites resulted in changing the second residue in the protein from glutamine to valine and adding a leucine and a glutamic acid residue to the C-terminus. The resulting DNA fragment was ligated into XhoI/NcoI-digested pSE280, creating pCPP2174, in which hrpN$_{Ech}$ was under control of the vector tac promoter. *E. chrysanthemi*

CUCPB5045(pCPP2174) and CUCPB5046(pCPP2174) possessed hypersensitive response elicitor activity (FIG. 5). Hypersensitive response elicitor activity could also be restored to these mutants by pCPP2142 and pCPP2171, but not by pCPP2141. Thus, the production of HrpN$_{Ech}$ is essential for elicitation of the hypersensitive response by *E. chrysanthemi* CUCPB5006.

The feasibility of testing the interchangeability of the hrpN genes of *E. chrysanthemi* and *E. amylovora* was supported by the observation that hypersensitive response elicitation activity could be restored to hrpN mutants in each species (*E. chrysanthemi* CUCPB5045 and *E. amylovora* Ea321T5) by their respective hrpN$^+$ subclones (pCPP2142 and pCPP1084). pCPP2142 was used for this purpose, because preliminary immunoblot experiments indicated that the level of hrpN$_{Ech}$ expression by this plasmid, though relatively high, most closely approximated expression of the native hrpN gene in *E. amylovora*. However, despite good heterologous expression of the hrpN genes, hypersensitive response elicitation activity was not restored in either *E. amylovora* Ea321T5(pCPP2142) or *E. chrysanthemi* (pCPP1084). Thus, the genes do not appear to be functionally interchangeable.

Example 10

*E. chrysantheml* hrpN$_{Ech}$ Mutants have a Reduced Ability to Incite Lesions in Witloof Chicory The hrpN$_{Ech}$439::Tn5-gusA1 mutation was marker-exchanged into the genome of wild-type strain AC4150. The resulting mutant, CUCPB5049, was analyzed for its virulence in witloof chicory. Leaves were inoculated at small wounds with 2×10$^4$ cells of mutant and wild-type strains, as previously described (Bauer, et al., "*Erwinia chrysanthemi* hr-p Genes and Their Involvement in Soft Rot Pathogenesis and Elicitation of the Hypersensitive Response," *Mol. Plant-Microbe Interact*, 7:573–581 (1994), which is incorporated by reference). The level of inoculum corresponded with the experimentally determined ED$_{50}$ of the wild-type strain for the batch of chicory heads used. The approximate surface area of macerated lesions was determined 72 hr after inoculation. The mutations did not abolish the pathogenicity of *E. chrysanthemi*, but significantly reduced the number of successful lesions (Table 2).

TABLE 2

Effects of hrpN$_{Ech}$ mutation on the ability of *Erwinia chrysanthemi* to incite lesions on witloof chicory leaves

| Strain | Number of lesions per 20 inoculations[a] | Size of lesions (mm$^2$, mean ± SD)[b] |
|---|---|---|
| AC4150 (wild type) | 16 | 80 ± 55 |
| CUCPB5049 (hrpn$_{Ech}$429::Tn5-gusA1) | 8[c] | 89 ± 42 |

[a]Each witloff chicory leaf was inoculated at two equivalent sites with 2 × 10$^4$ bacterial cells: one site received the hrpN$_{Ech}$ mutant, the other the parental wild-type strain; lesions were indicated by browning and maceration around the site of inoculation.
[b]Values represent the product of the length and width of the lesion.
[c]Different from the wild-type strain (P <0.05), as determined by the McNemar test (Conover, W. J., "Practial Nonparametric Statistics", 2 ed., John Wiley and Sons, New York (1980), which is incorporated by reference).

However, the hrpN$_{Ech}$ mutation had no significant effect on the size of the lesions produced in successful infections.

Example 11

Elicitation of a Rapid Necrosis in Several Plants by *E. chrysanthemi* is Dependent on HrpN$_{Ech}$ To determine whether *E. chrysanthemi* could cause a HrpN$_{Ech}$-dependent necrosis in plants other than tobacco, a variety of plants were infiltrated with purified HrpN$_{Ech}$ or inoculated with Pel-deficient *E. chrysanthemi* strains. The strains used were CUCPB5006 and its hrpN$_{Ech}$546::Tn5-gusA1 derivative CUCPB5045 and CUCPB5030 (ΔpelABCE outD::TnphoA) and its hrpN$_{Ech}$546::Tn5-gusA1 derivative CUCPB5063. The results with *Saintpaulia ionantha* are shown in FIG. 6 and for all plants are summarized in Table 3.

TABLE 3

Elicitation of necrosis in various plants by HrpN$_{Ech}$ and by *E. chrysanthemi* strains that are deficient in Pel production but not HrpN$_{Ech}$ production

| Plant | HrpN$_{Ech}$[a] | CUCPB5006 (ΔpelABCE)[b] | CUCPB5045 (ΔpelABCE hrpN$_{Ech}$546::Tn5-gusA1) | CUCPB5030 (ΔpelABCE outD::TnphoA) | CUCPB5063 (ΔpelABCE) outD::TnphoA hrpN$_{Ech}$546::Tn5-gusA1) |
|---|---|---|---|---|---|
| Tobacco | + | + | − | + | − |
| Tomato | + | + | − | + | − |
| Pepper | + | + | − | + | − |
| Saintpaulia | + | + | − | + | − |
| Petunia | + | + | − | + | − |
| Pelargonium | + | + | − | + | − |
| Squash | − | − | − | − | − |
| Zinnia | − | − | − | − | − |

[a]Leaves on plants were infiltrated with HrpN$_{Ech}$ at a concentration of 336 μg/ml and observed macroscopically 24 hr later for necrosis and collapse of the infiltrated area (+) or absence of any response (−).
[b]Leaves on plants were infiltrated with bacteria at a concentration of 5 × 10$^8$ and scored for responses as described above.

They yield several general observations. Plants responded either to both isolated HrpN$_{Ech}$ and hrpN$_{Ech}$ bacteria or to neither. Plants that responded to either treatment produced a nonmacerated, hypersensitive response-like necrosis that developed between 12 and 24 hr after infiltration. $hrpN_{Ech}$ mutants failed to elicit a response elicited in the plants tested, indicating that residual Pel isozymes or other proteins travelling the Out pathway were not involved in producing the hypersensitive response-like necrosis. The results argue that $HrpN_{Ech}$ is the only elicitor of the hypersensitive response produced by *E. chrysanthemi*.

*E. chrysanthemi* was found to produce a protein with many similarities to the harpin of *E. amylovora*. The two proteins share significant amino acid sequence identity, similar physical properties, and the ability to elicit the hypersensitive response in a variety of plants. Mutations in the $hrpN_{Ech}$ gene indicate that, as with *E. amylovora*, harpin production is required for elicitation of the hypersensitive response. Furthermore, both harpins contribute to bacterial pathogenicity, albeit to different degrees. $HrpN_{Ea}$ is essential for *E. amylovora* to produce symptoms in highly susceptible, immature pear fruit (Wei, et al. "Harpin, Elicitor of the Hypersensitive Response Produced by the Plant Pathogen *Erwinia amylovora*," *Science* 257:85–88 (1992), which is incorporated by reference), whereas $HrpN_{Ech}$ merely increases the frequency of successful *E. chrysanthemi* infections in susceptible witloof chicory leaves. Nevertheless, the finding that harpins play some role in the pathogenicity of such disparate pathogens suggests that these proteins have a conserved and widespread function in bacterial plant pathogenesis. We will consider below $HrpN_{Ech}$ with regard to the protein secretion pathways, extracellular virulence proteins, and wide host range of *E. chrysanthemi*.

*E. chrysanthemi* secretes proteins by multiple, independent pathways. Several protease isozymes are secreted by the Sec-independent (ABC-transporter or Type I) pathway; pectic enzymes and cellulase are secreted by the Sec-dependent (general secretion or Type II) pathway; and, $HrPN_{Ech}$ is likely to be secreted by the Sec-independent Hrp (Type III) pathway (Salmond, G. P. C., et al., "Secretion of Extracellular Virulence Factors by Plant Pathogenic Bacteria," *Annu. Rev. Phytopathol.* 32:181–200 (1994), which is incorporated by reference). The expectation that $HrpN_{Ech}$ is secreted by the Hrp pathway is supported by several lines of indirect evidence: (i) Hrp secretion pathway mutants have revealed that other members of this class of glycine-rich, heat-stable elicitor proteins, the *E. amylovora* $HrpN_{Ea}$, *P. syringae* pv. *syringae* HrpZ, and *P. solanacearum* PopA1 proteins, are secreted by this pathway (He, S. Y., et al., "*Pseudomonas syringae* pv. *syringae* $Harpin_{Pss}$: a Protein that is Secreted via the Hrp Pathway and Elicits the Hypersensitive Response in Plants," (1993); Wei, Z.-M., et al., "Hrpl of *Erwinia amylovora* Functions in Secretion of Harpin and is a Member of a New Protein Family", *J. Bacteriol.* 175:7958–7967 (1993); Arlat, M., et al. "PopA1, a Protein Which Induces a Hypersensitive-like Response on Specific Petunia Genotypes, is Secreted via the Hrp Pathway of *Pseudomonas solanacarum*," *EMBO J.* 13:543–553 (1994), which are hereby incorporated by reference); (ii) mutation of the *E. chrysanthemi* homolog of an *E. amylovora* gene involved in $HrpN_{Ea}$ secretion abolishes the ability of *E. chrysanthemi* to elicit the hypersensitive response, whereas mutation of the Out (Type II) pathway of *E. chrysanthemi* does not abolish the hypersensitive response; and (iii) $HrpN_{Ech}$ appears to be the only hypersensitive response elicitor produced by *E. chrysanthemi* (as discussed further below), suggesting that the effect of the putative hrp secretion gene mutation is on $HrpN_{Ech}$.

Attempts to demonstrate directly hrp-dependent secretion of $HrpN_{Ech}$ have been thwarted by apparent instability of the protein in *E. chrysanthemi*. Using the cell fractionation and immunoblotting procedures of He, S. Y., et al., "*Pseudomonas syringae* pv. *syringae* $Harpin_{Pss}$: a Protein that is Secreted via the Hrp Pathway and Elicits the Hypersensitive Response in Plants," *Cell* 73:1255–66 (1993), which is hereby incorporated by reference, and polyclonal anti-$HrpN_{Ea}$ antibodies that cross-react with $HrpN_{Ech}$ (Wei, Z.-M, et al., "Harpin, Elicitor of the Hypersensitive Response Produced by the Plant Pathogen *Erwinia amylovora*," *Science* 257:85–88 (1992), which is incorporated by reference), we have observed the presence of $HrpN_{Ech}$ in the cell-bound fraction of *E. chrysanthemi*. However, some culture preparations unexpectedly lack the protein, and no preparations reveal accumulation of the protein in the culture supernatant fraction. It is possible that $HrpN_{Ech}$ aggregates upon secretion and, therefore, precipitates from the medium. It is interesting that several of the Yersinia spp. Yop virulence proteins aggregate in the medium upon secretion via the Type III pathway (Michiels, T., et al., "Secretion of Yop Proteins by Yersiniae," *Infect. Immun.* 58:2840–2849 (1990), which is incorporated by reference). Similarly, $HrpN_{Ea}$ has a propensity to form aggregates or to associate with an insoluble membrane fraction (Wei, Z.-M, et al., "Harpin, Elicitor of the Hypersensitive Response Produced by the Plant Pathogen *Erwinia amylovora*," *Science* 257:85–88 (1992), which is incorporated by reference).

It is significant that there is little difference in the plant interaction phenotypes of *E. chrysanthemi* mutants deficient in either $HrpN_{Ech}$ or a putative component of the Hrp secretion pathway (Bauer, D. W., et al., "*Erwinia chrysanthemi* hrp Genes and Their Involvement in Soft Rot Pathogenesis and Elicitation of the Hypersensitive Response," *Mol. Plant-Microbe Interact*, 7:573–581 (1994), which is incorporated by reference). Both mutations abolish the ability of Pel-deficient strains to elicit the hypersensitive response, and they both reduce the frequency of successful infections incited by fully pectolytic strains in witloof chicory leaves without affecting the size of the macerated lesions that do develop. This pattern contrasts with that observed with mutations affecting Pel isozymes and the Out pathway. Maceration virulence is merely reduced by individual pel mutations, whereas it is abolished by out mutations. This is because multiple Pel isozymes (and possibly other enzymes) contribute quantitatively to virulence, but all of the Pel isozymes appear to be dependent on the Out pathway for secretion from the bacterial cell. The simplest interpretation of the observations with *E. chrysanthemi* hrp mutants is that $HrpN_{Ech}$ is the only protein travelling the Hrp pathway that has a detectable effect on the interaction of *E. chrysanthemi* EC16 with the plants tested.

The primacy of $HrpN_{Ech}$ in the *E. chrysanthemi* Hrp system is further supported by the observations that $hrpN_{Ech}$ mutants failed to elicit necrosis in any of the several plants tested and that all plants responding with apparent hypersensitivity to $HrpN_{Ech}^+$ strains also responded to isolated $HrpN_{Ech}$. Several of the plants sensitive to $HrpN_{Ech}$ are also susceptible to bacterial soft rots. This is particularly significant for Saintpaulia, whose interactions with *E. chrysanthemi* have been extensively studied (Barras, F., et al., "Extracellular Enzymes and Pathogenesis of Soft-rot Erwinia," *Annu. Rev. Phytopathol.* 32:201–234 (1994), which is hereby incorporated by reference). Thus, $HrpN_{Ech}$ elicits hypersensitive response-like responses in plants that are susceptible to *E. chrysanthemi* infections under appropriate environmental conditions. The significance of this for the wide host range of the bacterium requires further investigation, and virulence tests with hrpN$_{Ech}$ mutants and additional susceptible plants are needed to determine the general importance of HrpN$_{Ech}$ and the Hrp system in *E. chrysanthemi*. For example, the present data do not address the possibility that other proteins secreted by the Hrp pathway, which are not elicitors of the hypersensitive response in the plants tested, may contribute to pathogenesis in hosts other than witloof chicory.

An important question is whether bacteria expressing heterologous harpins will be altered in pathogenicity. The hrpN genes of *E. chrysanthemi* and *E. amylovora* are particularly attractive for experiments addressing this because of the similarity of the harpins and the dissimilarity of the diseases produced by these bacteria. Unfortunately, attempts to restore the hypersensitive response phenotype to *E. chrysanthemi* and *E. amylovora* hrpN mutants with heterologous hrpbr subclones failed. Since the hrpN genes in each subclone successfully complemented hrpN mutations in homologous bacteria and were expressed in heterologous bacteria, the problem is most likely the secretion of the harpins by heterologous Hrp systems. A similar problem has been encountered with heterologous secretion of Pel and cellulase via the Out pathway in *E. chxysanthemi* and *E. carotovora*, species that are more closely related to each other in this rather heterogenous genus than are *E. chrysanthemi* and *E. amylovora* (He, S. Y., et al., "Cloned *Erwinia chrysanthemi* out Genes Enable *Escherichia coli* to Selectively Secrete a Diverse Family of Heterologous Proteins to its Milieu," *Proc. Natl. Acad. Sci. U.S.A.* 88:1079–1083 (1991); Py, B., et al., "Secretion of Cellulases in *Erwinia chrysanthemi* and *E. carotovora* is Species-specific," *FEMS Microbiol. Lett.* 79:315–322 (1991), which are hereby incorporated by reference).

In conclusion, two classes of proteins contribute to the pathogenicity of *E. chrysanthemi*—a single harpin and a battery of plant cell wall-degrading pectic enzymes. The observation that such a highly pectolytic organism also produces a harpin suggests the fundamental importance of harpins in the pathogenicity of gram-negative bacteria. The observation that a hrpN$_{Ech}$::Tn5-gusA1 mutation reduced the ability of a fully pectolytic strain of *E. chrysanthemi* to initiate lesions in susceptible chicory leaves, but did not reduce the size of lesions that did develop, suggests that HrpN$_{Ech}$ contributes specifically to an early stage of pathogenesis. An attractive possibility is that HrpN$_{Ech}$ releases nutrients to the apoplast for bacterial nutrition before the pel genes are fully expressed (Collmer, A., et al., "*Erwinia chrysanthemi* and *pseudomonas syringae*: Plant Pathogens Trafficking in Virulence Proteins," pages 43–78 in: *Current Topics in Microbiology and Immunology*, Vol. 192: *Bacterial Pathogenesis of Plants and Animals—Molecular and Cellular Mechanisms* (1994), which is incorporated by reference). Patterns of pel and hrpN$_{Ech}$ expression in plants will likely yield further clues to the role of the *E. chrysanthemi* harpin in soft rot pathogenesis.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated protein or polypeptide from *Erwinia chrysanthemi* which elicits a hypersensitive response in plants, wherein the isolated protein or polypeptide has an amino acid sequence of SEQ. ID. No. 2.

2. An isolated protein or polypeptide according to claim 1, wherein the protein or polypeptide has a molecular weight of 32 to 36 kDa.

3. An isolated protein or polypeptide according to claim 1, wherein the protein or polypeptide is heat stable, has a glycine content of greater than 16%, and contains no cysteine.

4. An isolated protein or polypeptide according to claim 1, wherein the protein or polypeptide is purified.

5. An isolated protein or polypeptide according to claim 1, wherein the protein or polypeptide is recombinant.

* * * * *